US007700720B2

(12) United States Patent
Tous et al.

(10) Patent No.: US 7,700,720 B2
(45) Date of Patent: Apr. 20, 2010

(54) ANTIBODIES AGAINST AND METHODS FOR PRODUCING VACCINES FOR RESPIRATORY SYNCYTIAL VIRUS

(75) Inventors: Guillermo Tous, East Windsor, NJ (US); Mark Schenerman, Reisterstown, MD (US); Jose Casas-Finet, Gaithersburg, MD (US); Ziping Wei, North Potomac, MD (US); David Pfarr, Darnestown, MD (US)

(73) Assignee: MedImmune, LLC, Gaithersburg, MD (US)

( * ) Notice: Subject to any disclaimer, the term of this patent is extended or adjusted under 35 U.S.C. 154(b) by 921 days.

(21) Appl. No.: 11/230,593

(22) Filed: Sep. 21, 2005

(65) Prior Publication Data

US 2006/0099220 A1 May 11, 2006

Related U.S. Application Data

(60) Provisional application No. 60/611,313, filed on Sep. 21, 2004.

(51) Int. Cl.
*A61K 39/155* (2006.01)
*C07K 14/115* (2006.01)
*C07K 19/00* (2006.01)

(52) U.S. Cl. ................ 530/325; 424/184.1; 424/185.1; 424/192.1; 424/211.1; 530/300

(58) Field of Classification Search .................. 530/300
See application file for complete search history.

(56) References Cited

U.S. PATENT DOCUMENTS 5,149,650 A 9/1992 Wertz et al.
5,223,254 A * 6/1993 Paradiso et al. .......... 424/186.1
5,824,307 A 10/1998 Johnson
2002/0018780 A1 2/2002 Koenig

FOREIGN PATENT DOCUMENTS

WO WO0189562 A1 11/2001

OTHER PUBLICATIONS

Dennis et al., J. Biol. Chem., vol. 277, Issue 38, 35035-35043, Sep. 20, 2002 Albumin binding as a general strategy for improving the pharmacokinetics of proteins.*

Anderson, et al., "Identification of Epitopes on Respiratory Syncytial Virus Proteins by Competitive Binding Immunoassay", Journal of Clinical Microbiology, 1986, p. 475-480, vol. 23(3).

Arbiza, et al., "Characterization of two antigenic sites recognized by neutralizing monoclonal antibodies directed against the fusion glycoprotein of human respiratory syncytial virus", Journal of General Virology, 1992, p. 2225-2234, vol. 73.

Beeler, et al., "Neutralization Epitopes of the F Glycoprotein of Respiratory Syncytial Virus: Effect of Mutation upon Fusion Function", Journal of Virology, 1989, p. 2941-2950, vol. 63(7).

Johnson, et al., "Development of a Humanized Monoclonal Antibody (MEDI-493) with Potent In Vitro and In Vivo Activity against Respiratory Syncytial Virus", The Journal of Infectious Diseases, 1997, p. 1215-1224, vol. 176.

Lopez, et al. "Conformational constraints of conserved neutralizing epitopes from a major antigenic area of human respiratory syncytial virus fusion glycoprotein", Journal of General Virology, 1993, p. 2567-2577, vol. 74.

Lopez, et al., "Antigenic Structure of Human Respiratory Syncytial Virus Fusion Glycoprotein", Journal of Virology, 1998 p. 6922-6928, vol. 72(8).

Trudel, et al., "Identification of a Synthetic Peptide as Part of a Major Neutralization Epitope of Respiratory Syncytial Virus", Journal of General Virology, 1987, p. 2273-2280, vol. 68.

Crowe, Jr. J.E., 1998, "Isolation of a Second Recombinant Human Respiratory Syncytial Virus Monoclonal Antibody Fragment (Fab RSVF2-5) that Exhibits Therapeutic Efficacy In Vivo", The Journal of Infectious Diseases, 177(4):1073-1076.

Dennis, Mark S. et al., Sep. 20, 2002, "Albumin Binding as a General Strategy for Improving the Pharmacokinetics of Proteins," The Journal Of Biological Chemistry, 277(38):35035-35043.

Dennis, et al., "Albumin Binding as a General Strategy for Improving the Pharmacokinetics of Proteins", The Journal of Biological Chemistry, 277:38, 35035-35043.

* cited by examiner

*Primary Examiner*—Mary E Mosher
*Assistant Examiner*—Myron G Hill

(57) ABSTRACT

The present invention relates to novel respiratory syncytial virus (RSV) F peptides and compositions comprising them. The present invention also relates to methods of evaluating anti-RSV antibody binding to F peptides. The present invention also relates to antibodies that immunospecifically bind to an F peptide of the present invention. The invention further provides methods and protocols for the administration of F peptides and/or antibodies that immunospecifically bind to F peptides for the prevention, neutralization, treatment of RSV infection. Additionally, the methods of the invention may be useful for the treatment, prevention and the amelioration of symptoms associated with RSV infection.

15 Claims, 5 Drawing Sheets

FIGURE 1

```
MELPILKANA ITTILAAVTF CFASSQNITE EFYQSTCSAV SKGYLSALRT GWYTSVITIE   60
LSNIKENKCN GTDAKVKLIK QELDKYKNAV TELQLLMQST PAANNRARRE LPRFMNYTLN  120
NTKKTNVTLS KKRKRRFLGF LLGVGSAIAS GTAVSKVLHL EGEVNKIKSA LLSTNKAVVS  180
LSNGVSVLTS KVLDLKNYID KQLLPIVNKQ SCRISNIETV IEFQQKNNRL LEITREFSVN  240
AGVTTPVSTY MLTNSELLSL INDMPITNDQ KKLMSNNVQI VRQQSYSIMS IIKEEVLAYV  300
VQLPLYGVID TPCWKLHTSP LCTTNTKEGS NICLTRTDRG WYCDNAGSVS FFPQAETCKV  360
QSNRVFCDTM NSLTLPSEVN LCNVDIFNPK YDCKIMTSKT DVSSSVITSL GAIVSCCYGK  420
TKCTASNKNR CIIKTFSNGC DYASNKGVDT VSVGNTLYYV NKQEGKSLYV KGEPIINFYT  480
PLVFPSDEFD ASISQVNEKI NQSLAFIRKS DELLHHVNAG KSTTNIMITT IIIVIIVILL  540
SLIAVGLLLY CKARSTPVTL SKDQLSGINN IAFSN                             575
```

ANTIBODIES AGAINST AND METHODS FOR PRODUCING VACCINES FOR RESPIRATORY SYNCYTIAL VIRUS

CROSS REFERENCE TO RELATED APPLICATIONS

This application claims the benefit under 35 U.S.C. §119 (e) of U.S. Provisional Application No. 60/611,313, filed Sep. 21, 2004, which is hereby incorporated by reference herein in its entirety for all purposes.

FIELD OF THE INVENTION

The present invention relates to pharmaceutical compositions comprising a respiratory syncytial virus (RSV) F protein epitope (exemplified by SEQ ID NO.:1) and variants thereof or F peptides. In one embodiment, the RSV F protein epitope (or variant thereof) or F peptide immunospecifically binds the monoclonal antibody SYNAGIS® and/or NUMAX™. In another embodiment, an RSV F peptide or F protein epitope of the invention binds a native RSV receptor on the surface of mammalian host cells. The invention further includes methods for preventing, treating or ameliorating symptoms associated with respiratory syncytial virus (RSV) infection utilizing said compositions. In particular, the present invention relates to methods for preventing, treating or ameliorating symptoms associated with RSV infection, wherein said methods comprise administering to a human subject an effective amount of one or more RSV F peptides or F protein epitopes (or variants or fragments thereof) that effectively prevent RSV infection. The present invention further relates to methods of evaluating anti-RSV antibody binding to F protein epitope variants (i.e., F peptides). The present invention also relates to antibodies or fragments thereof, that immunospecifically bind to an RSV F peptide of the invention or an F protein epitope and methods for screening for and detecting such antibodies and utilizing said antibodies, wherein such antibodies are not Synagis® (palivizumab) or Numax™ (motavizumab) or murine mAbs 47F and 7C2 (see, Arbiza J. et al., J. Gen. Virol., 73:2225-2234 (1992)).

BACKGROUND OF THE INVENTION

Respiratory syncytial virus (RSV) is the leading cause of serious lower respiratory tract disease in infants and children (Feigen et al., eds., 1987, In: *Textbook of Pediatric Infectious Diseases*, W B Saunders, Philadelphia at pages 1653-1675; *New Vaccine Development, Establishing Priorities*, Vol. 1, 1985, National Academy Press, Washington D.C. at pages 397-409; and Ruuskanen et al., 1993, *Curr. Probl. Pediatr.* 23:50-79). The yearly epidemic nature of RSV infection is evident worldwide, but the incidence and severity of RSV disease in a given season vary by region (Hall, C. B., 1993, *Contemp. Pediatr.* 10:92-110). In temperate regions of the northern hemisphere, it usually begins in late fall and ends in late spring. Primary RSV infection occurs most often in children from 6 weeks to 2 years of age and uncommonly in the first 4 weeks of life during nosocomial epidemics (Hall et al., 1979, *New Engl. J. Med.* 300:393-396). Children at increased risk from RSV infection include preterm infants (Hall et al., 1979, *New Engl. J. Med.* 300:393-396) and children with bronchopulmonary dysplasia (Groothuis et al., 1988, *Pediatrics* 82:199-203), congenital heart disease (MacDonald et al., *New Engl. J. Med.* 307:397-400), congenital or acquired immunodeficiency (Ogra et al., 1988, *Pediatr. Infect. Dis. J.* 7:246-249; and Pohl et al., 1992, *J. Infect. Dis.* 165:166-169), and cystic fibrosis (Abman et al., 1988, *J. Pediatr.* 113:826-830). The fatality rate in infants with heart or lung disease who are hospitalized with RSV infection is 3%-4% (Navas et al., 1992, *J. Pediatr.* 121:348-354).

RSV infects adults as well as infants and children. In healthy adults, RSV causes predominantly upper respiratory tract disease. It has recently become evident that some adults, especially the elderly, have symptomatic RSV infections more frequently than had been previously reported (Evans, A. S., eds., 1989, *Viral Infections of Humans. Epidemiology and Control,* 3.sup.rd ed., Plenum Medical Book, New York at pages 525-544). Several epidemics also have been reported among nursing home patients and institutionalized young adults (Falsey, A. R., 1991, *Infect. Control Hosp. Epidemiol.* 12:602-608; and Garvie et al., 1980, *Br. Med. J.* 281:1253-1254). Finally, RSV may cause serious disease in immunosuppressed persons, particularly bone marrow transplant patients (Hertz et al., 1989, *Medicine* 68:269-281).

Treatment options for established RSV disease are limited. Severe RSV disease of the lower respiratory tract often requires considerable supportive care, including administration of humidified oxygen and respiratory assistance (Fields et al., eds, 1990, *Fields Virology,* $2^{nd}$ ed., Vol. 1, Raven Press, New York at pages 1045-1072). The only drug approved for treatment of infection is the antiviral agent ribavirin (American Academy of Pediatrics Committee on Infectious Diseases, 1993, *Pediatrics* 92:501-504). It has been shown to be effective in the treatment of RSV pneumonia and bronchiolitis, modifying the course of severe RSV disease in immunocompetent children (Smith et al., 1991, *New Engl. J. Med.* 325:24-29). However, ribavirin has had limited use because it requires prolonged aerosol administration and because of concerns about its potential risk to pregnant women who may be exposed to the drug during its administration in hospital settings.

While a vaccine might prevent RSV infection, no commercially available vaccine is yet licensed for this indication. A major obstacle to vaccine development is safety. A formalin-inactivated vaccine, though immunogenic, unexpectedly caused a higher and more severe incidence of lower respiratory tract disease due to RSV in immunized infants than in infants immunized with a similarly prepared trivalent parainfluenza vaccine (Kim et al., 1969, *Am. J. Epidemiol.* 89:422-434; and Kapikian et al., 1969, *Am. J. Epidemiol.* 89:405-421). Several candidate RSV vaccines have been abandoned and others are under development (Murphy et al., 1994, *Virus Res.* 32:13-36), but even if safety issues are resolved, vaccine efficacy must also be improved. A number of problems remain to be solved. Immunization would be required in the immediate neonatal period since the peak incidence of lower respiratory tract disease occurs at 2-5 months of age. The immaturity of the neonatal immune response together with high titers of maternally acquired RSV antibody may be expected to reduce vaccine immunogenicity in the neonatal period (Murphy et al., 1988, *J. Virol.* 62:3907-3910; and Murphy et al., 1991, *Vaccine* 9:185-189). Finally, primary RSV infection and disease do not protect well against subsequent RSV disease (Henderson et al., 1979, *New Engl. J. Med.* 300:530-534).

Currently, the only approved approach to prophylaxis of RSV disease is passive immunization. Initial evidence suggesting a protective role for IgG was obtained from observations involving maternal antibody in ferrets (Prince, G. A., Ph.D. diss., University of California, Los Angeles, 1975) and humans (Lambrecht et al, 1976, *J. Infect. Dis.* 134:211-217; and Glezen et al., 1981, *J. Pediatr.* 98:708-715). Hemming et al. (Morell et al., eds., 1986, *Clinical Use of Intravenous*

*Immunoglobulins*, Academic Press, London at pages 285-294) recognized the possible utility of RSV antibody in treatment or prevention of RSV infection during studies involving the pharmacokinetics of an intravenous immune globulin (IVIG) in newborns suspected of having neonatal sepsis. They noted that 1 infant, whose respiratory secretions yielded RSV, recovered rapidly after IVIG infusion. Subsequent analysis of the IVIG lot revealed an unusually high titer of RSV neutralizing antibody. This same group of investigators then examined the ability of hyperimmune serum or immune globulin, enriched for RSV neutralizing antibody, to protect cotton rats and primates against RSV infection (Prince et al., 1985, *Virus Res.* 3:193-206; Prince et al., 1990, *J. Virol.* 64:3091-3092; Hemming et al., 1985, *J. Infect. Dis.* 152: 1083-1087; Prince et al., 1983, *Infect. Immun.* 42:81-87; and Prince et al., 1985, *J. Virol.* 55:517-520). Results of these studies suggested that RSV neutralizing antibody given prophylactically inhibited respiratory tract replication of RSV in cotton rats. When given therapeutically, RSV antibody reduced pulmonary viral replication both in cotton rats and in a nonhuman primate model. Furthermore, passive infusion of immune serum or immune globulin did not produce enhanced pulmonary pathology in cotton rats subsequently challenged with RSV.

Two glycoproteins, F and G, on the surface of RSV have been shown to be targets of neutralizing antibodies (Fields et al., 1990, supra; and Murphy et al., 1994, supra). These two proteins are also primarily responsible for viral recognition and entry into target cells; G protein binds to a specific cellular receptor and the F protein promotes fusion of the virus with the cell. The F protein is also expressed on the surface of infected cells and is responsible for subsequent fusion with other cells leading to syncytia formation. Thus, antibodies to the F protein may directly neutralize virus or block entry of the virus into the cell or prevent syncytia formation. Although antigenic and structural differences between A and B subtypes have been described for both the G and F proteins, the more significant antigenic differences reside on the G glycoprotein, where amino acid sequences are only 53% homologous and antigenic relatedness is 5% (Walsh et al., 1987, *J. Infect. Dis.* 155:1198-1204; and Johnson et al., 1987, *Proc. Natl. Acad. Sci. USA* 84:5625-5629). Conversely, antibodies raised to the F protein show a high degree of cross-reactivity among subtype A and B viruses. Beeler and Coelingh (1989, *J. Virol.* 7:2941-2950) conducted an extensive analysis of 18 different murine MAbs directed to the RSV F protein. Comparison of the biologic and biochemical properties of these MAbs resulted in the identification of three distinct antigenic sites (designated A, B, and C). Neutralization studies were performed against a panel of RSV strains isolated from 1956 to 1985 that demonstrated that epitopes within antigenic sites A and C are highly conserved, while the epitopes of antigenic site B are variable.

Thus protective response against RSV is contingent on the production of neutralizing antibodies against the major viral surface glycoproteins while minimizing non-protective or pathological immune responses. The present invention avoids such problems by providing a vaccine that comprises a peptide epitope within the F protein structure (SEQ ID No.29) that have been shown to specifically interact with known potent neutralizing antibodies. This epitope can be used as a vaccine against the RSV infections and/or be used to immunize mammals to create antibodies for the use of preventing or treating RSV infections and/or used as a passive therapy in order to prevent RSV from binding to its receptor.

The humanized antibody, SYNAGIS® which immunospecifically binds to the F protein epitope of SEQ ID NO: 1, is approved for intramuscular administration to pediatric patients for prevention of serious lower respiratory tract disease caused by RSV at recommended monthly doses of 15 mg/kg of body weight throughout the RSV season (November through April in the northern hemisphere). SYNAGIS® is a composite of human (95%) and murine (5%) antibody sequences. See, Johnson et al., 1997, *J. Infect. Diseases* 176: 1215-1224 and U.S. Pat. No. 5,824,307, the entire contents of which are incorporated herein by reference. The human heavy chain sequence was derived from the constant domains of human $IgG_1$ and the variable framework regions (VH) from Cor (Press et al., 1970, *Biochem. J.* 117:641-660) and Cess (Takashi et al., 1984, *Proc. Natl. Acad. Sci. USA* 81:194-198). The human light chain sequence was derived from the constant domain of Cκ and the variable framework regions of the VL gene K104 with Jκ −4 (Bentley et al., 1980, *Nature* 288:5194-5198). The murine sequences were derived from a murine monoclonal antibody, Mab 1129 (Beeler et al., 1989, *J. Virology* 63:2941-2950), in a process which involved the grafting of the murine complementarity determining regions into the human antibody frameworks.

Although SYNAGIS® has been successfully used for the prevention of RSV infection in pediatric patients, multiple intramuscular doses of 15 mg/kg of SYNAGIS® are required to achieve a prophylactic effect. The necessity for the administration of multiple intramuscular doses of antibody requires repeated visits to the doctors office which is not only inconvenient for the patient but can also result in missed doses. Thus, a need exists for antibodies that immunospecifically bind to a RSV antigen, which are highly potent, have an improved pharmacokinetic profile, and thus have an overall improved therapeutic profile. In U.S Patent Publication 2003/0091584 a more potent anti-RSV molecule, NUMAX™, is disclosed. NUMAX™ has improved binding characteristics that may overcome the higher dosing requirements described supra.

In general, the manufacturing of antibodies is very expensive and the amount of antibody that can be purified and concentrated is limited by the nature of the molecule. Thus, the need exists to produce a molecule that has the same effect as SYNAGIS®, while being less costly to produce and more readily concentrated. In addition, there is a need to prevent RSV infection proactively via immunizations, either active or passive, in order to prevent an RSV infection.

Citation or discussion of a reference herein shall not be construed as an admission that such is prior art to the present invention.

SUMMARY OF THE INVENTION

The present invention is based, in part, on the discovery of the RSV F protein epitope (alternatively, F protein epitope), that the antibody SYNAGIS® specifically binds. The F protein epitope comprises a 24 amino acid sequence: NSELLSLINDMPITNDQKKLMSNN (SEQ ID NO: 1) which competitively inhibits SYNAGIS® binding to the F-protein of RSV. One embodiment of the invention is a method of utilizing the F protein epitope and/or fragments, derivatives, and variants thereof (termed "F peptides") for generating (in-vivo, ex-vivo, or in-vitro) neutralizing antibodies (or other molecules that specifically bind the F protein epitopes or F peptides of the invention) against respiratory syncytial virus (RSV). Another embodiment of the invention is a method of administering a pharmaceutical composition comprising one or more F protein epitope and/or F peptides of the invention to a human in order to inhibit the binding of the RSV virus to its natural receptor and/or to be provided as a vaccine for preventing infection. Yet another embodiment of the invention relates to a method of treating upper respiratory tract infection caused by RSV in a patient/subject in need thereof comprising, intranasally administering an effective amount of a pharmaceutical composition of either the antibodies of the invention or the F peptides of the invention.

Another embodiment of the present invention is a method of screening for molecules including, but not limited to, antibodies, aptamers, small molecules (generally considered less than 10 kD in size), peptides (including fragments and derivatives of the foregoing) that specifically bind one or more F protein epitope or F peptides of the invention (collectively herein, "anti-F peptide binders" or "anti-F binders" or "anti-F peptide antibodies"). It is specifically contemplated that such screening methods would be used to identify molecules that neutralize RSV and/or prevent syncytia formation. In yet another embodiment, the F peptides are useful for the generation of binders, e.g., antibodies that specifically bind to an F peptide. Antibodies, fragments and derivatives thereof that specifically bind to an F protein epitope or F peptide are referred to herein as "anti-F protein antibodies or anti-F peptide antibodies", respectively.

The present invention encompasses, but is not limited to, recombinant, fully human, chimeric, mouse, CDR-grafted, and humanized anti-F protein antibodies or anti-F peptide antibodies and fragments and derivatives thereof, which are more fully described below.

F peptides of the invention are at least 50%, or at least 60%, or at least 70%, or at least 80%, or at least 90%, or at least 95%, or at least 99%, or at least 99.5% identical to the F protein epitope of SEQ ID NO: 1.

The F protein epitopes and F peptides may be derived from the A antigenic region of the F protein (see FIG. 1). As used herein, the term "derived" includes sequences similar but not identical to the sequence of the protein disclosed herein and to fragments sequences otherwise identical to the sequences of said protein. Also included are derivatives of the F protein epitope and/or F peptides including but not limited to, methylated, acetylated, carboxylated, glycosylated, and those containing non-natural amino acids.

It is another object of the present invention to provide F protein epitope and/or F peptides as heterologous polypeptide segments (e.g., as part of a fusion and/or chimeric molecule), or fragment, or portion thereof.

In one embodiment, the F protein epitopes and Fpeptides of the invention are recognized by the humanized antibody whose amino acid sequence is disclosed in Johnson et al., J. Infect. Dis. 176:1215-1224 (1997), including the modified humanized recombinant antibody referred to herein as SYNAGIS® (palivizumab).

In another embodiment, the F protein epitopes and F peptides of the invention are recognized by the humanized antibody whose amino acid sequence is disclosed in U.S. Pat. No. 6,818,216, including the modified humanized recombinant IgG1 antibody referred to herein as NUMAX™ (motavizumab) or MEDI-524.

In yet another embodiment, the F protein epitopes and F peptides of the invention are recognized by an anti-RSV antibody or fragment thereof that is not SYNAGIS® or NUMAX™ or the murine mAbs 47F and 7C2 (see, Arbiza J. et al., J. Gen. Virol., 73:2225-2234 (1992)).

While it is to be understood that the F protein epitopes and F peptides of the invention may bind to SYNAGIS® and/or NUMAX™ or the murine mAbs 47F and 7C2it is also to be understood that F protein epitopes and F peptides may bind to antibodies or fragments thereof, other than SYNAGIS® or NUMAX™ or the murine mAbs 47F and 7C2See, examples in U.S. Pat. No. 5,762,905; U.S. Pat. No. 5,811,534; U.S Patent Publication 2003/0091584; Beeler et al. (1989, *J. Virol* 63: 2941); and Palomo et al., 1990, *J. Virol* 64: 4199) each of which are incorporated herein by reference. The skilled artisan will further appreciate that the F protein epitopes and F peptides may bind to chimeric, humanized, fully human, CDR-grafted, and other derivatives of an antibody other than SYNAGIS® or NUMAX™ that immunospecifically binds to an F protein epitope and/or F peptide.

It is a further object of the present invention to provide an pharmaceutical composition comprising at least one F protein epitope and/or F peptide binder, wherein said binder is suspended in a pharmacologically acceptable carrier. Acceptable pharmaceutical carriers include but are not limited to non-toxic buffers, fillers, isotonic solutions, etc. Additionally, vaccines, or vaccine compositions, comprising said peptide are contemplated as an embodiment of the invention.

It is a still further object of the present invention to provide a process for preventing or treating an RSV infection comprising administering to a patient in need of such prevention or treatment, a therapeutically, or prophylactically, effective amount of a vaccine composition comprising the immunogenic composition described above.

It is a further object of the present invention to provide an immunogenic composition comprising at least one F protein epitope and/or F peptide of the invention wherein said peptide is suspended in a pharmacologically acceptable carrier. Acceptable pharmaceutical carriers include but are not limited to non-toxic buffers, fillers, isotonic solutions, etc. Additionally, vaccines, or vaccine compositions, comprising said peptide are contemplated as an embodiment of the invention.

The present invention provides methods of preventing, neutralizing, treating and ameliorating one or more symptoms associated with RSV infection in a subject comprising administering to said subject one or more of the F protein epitope and/or F peptides of the invention or fragments thereof. It is further contemplated that such administration be either intranasal or inhaled (pulmonary).

The present invention also provides methods of preventing, neutralizing, treating and ameliorating one or more symptoms associated with RSV infection in a subject comprising administering to said subject one or more of the anti-RSV antibodies or fragments thereof obtained by using the F protein epitopes or F peptides of the invention or fragments thereof. It is also contemplated that the present invention also provides methods of preventing, neutralizing, treating and ameliorating one or more symptoms associated with RSV infection in a subject comprising administering to said subject one or more of the anti-RSV antibodies or fragments thereof obtained by using the F protein epitopes or F peptides of the invention or fragments thereof, wherein the anti-RSV antibodies or fragments thereof are not SYNAGIS® or NUMAX™ or murine mAbs 47F and 7C2 (see, Arbiza J. et al., J. Gen. Virol., 73:2225-2234 (1992)). It is further contemplated that such administration be either intranasal or inhaled (pulmonary).

The invention encompasses sustained release formulations for the administration of one or more of the F protein epitopes or F peptides and fragments thereof. The sustained release formulations reduce the dosage and/or frequency of administration of said peptides to a subject. Further, the sustained release formulations may be administered to maintain a therapeutically or prophylactically effective serum titer which does not exceed a certain maximum serum titer for a certain period of time.

The invention encompasses sustained release formulations for the administration of one or more anti-F peptide or F protein epitope binders (e.g., antibodies or fragments thereof) wherein the anti-RSV antibodies or fragments thereof are not SYNAGIS® or NUMAX™ or murine mAbs 47F and 7C2 (see, Arbiza J. et al., *J. Gen. Virol.,* 73:2225-2234 (1992)). The sustained release formulations of the invention reduce the dosage and/or frequency of administration of said binders to a subject. Further, the sustained release formulations may be administered to maintain a therapeutically or prophylactically effective serum levels (e.g., titer) which does not exceed a certain maximum serum titer for a certain period of time.

The present invention encompasses methods of administering an F protein epitope or Fpeptide of the invention and/or anti-F protein epitope or F peptide binders (e.g., antibodies) directly to the site of RSV infection. In particular, the invention encompasses pulmonary or intranasal delivery of at least one F protein epitope or F peptide of the invention and/or one or more anti-F protein epitope or F peptide binder (e.g., antibodies). As an example, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety. In one embodiment, an antibody of the invention or fragment thereof, or composition of the invention is administered using Alkermes AIR.™. pulmonary drug delivery technology (Alkermes, Inc., Cambridge, Mass.). Alternatively, methods of administering an antibody or fragment thereof, or pharmaceutical composition include, but are not limited to, parenteral administration (e.g., intradermal, intramuscular, intraperitoneal, intravenous and subcutaneous), epidural, and mucosal (e.g., intranasal and oral routes). In one embodiment, antibodies of the present invention or fragments thereof, or pharmaceutical compositions are administered intramuscularly, intravenously, or subcutaneously. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The present invention also provides antibodies or fragments thereof that immunospecifically bind the F protein epitope of SEQ ID NO:1 and/or an 80% identical F peptide variant thereof and have an association rate constant or $k_{on}$ rate (antibody (Ab)+antigen (Ag) Ab-Ag) of at least $10^5$ $M^{-1}$ $s^{-1}$, at least $5\times10^5$ $M^{-1}$ $s^{-1}$, at least $10^6$ $M^{-1}$ $s^{-1}$, at least $5\times10^6$ $M^{-1}$ $s^{-1}$, at least $10^7$ $M^{-1}$ $s^{-1}$, at least $5\times10^7$ $M^{-1}$ $s^{-1}$, or at least $10^8$ $M^{-1}$ $s^{-1}$ as assessed using an assay described herein or known to one of skill in the art (e.g., a BIAcore assay)

The present invention provides antibodies or fragments thereof that specifically bind the F protein epitope of SEQ ID NO: 1 and/or an 80% identical F peptide variant thereof and have a $k_{off}$ rate (antibody (Ab)+antigen (Ag) Ab-Ag) of less than $10^{-1}$ $s^{-1}$, less than $5\times10^{-1}$ $s^{-1}$, less than $10^{-2}$ $s^{-1}$, less than $5\times10^{-2}$ $s^{-1}$, less than $10^{-3}$ $s^{-1}$, less than $5\times10^{-3}$ $s^{-1}$, less than $10^{-4}$ $s^{-1}$, less than $5\times10^{-4}$ $s^{-1}$, less than $10^{-5}$ $s^{-1}$, less than $5\times10^{-5}$ $s^{-1}$, less than $10^{-6}$ $s^{-1}$, less than $5\times10^{-6}$ $s^{-1}$, less than $10^{-7}$ $s^{-1}$, less than $5\times10^{-7}$ $s^{-1}$, less than $10^{-8}$ $s^{-1}$, less than $5\times10^{-8}$ $s^{-1}$, less than $10^{-9}$ $s^{-1}$, less than 5.times.$10^{-9}$ $s^{-1}$, or less than $10^{-10}$ $s^{-1}$ as assessed using an assay described herein or known to one of skill in the art (e.g., a BIAcore assay)

The present invention also provides antibodies or fragments thereof that specifically bind the F protein epitope of SEQ ID NO:1 and/or an 80% identical F peptide variant thereof and have an affinity constant or $K_a$ ($k_{on}/k_{off}$) of at least $10^2$ $M^{-1}$, at least $5\times10^2$ $M^{-1}$, at least $10^3$ $M^{-1}$, at least $5\times10^3M^{-1}$, at least $10^4$ $M^{-1}$, at least $5\times10^4$ $M^{-1}$, at least $10^5$ $M^{-1}$, at least $5\times10^5$ $M^{-1}$, at least $10^6$ $M^{-1}$, at least $5\times10^6$ $M^{-1}$, at least $10^7$ $M^{-1}$, at least $5\times10^7$ $M^{-1}$, at least $10^8$ $M^{-1}$, at least $5\times10^8$ $M^{-1}$, at least $10^9$ $M^{-1}$, at least $5\times10^9$ $M^{-1}$, at least $10^{10}$ $M^{-1}$, at least $5\times10^{10}$ $M^{-1}$, at least $10^{11}$ $M^{-1}$, at least $5\times10^{12}$ $M^{-1}$, at least $10^{12}M^{-1}$, at least $5\times10^{12}$ $M^{-1}$, at least $10^{13}$ $M^{-1}$, at least $5\times10^{13}$ $M^{-1}$, at least $10^{14}$ $M^{-1}$, at least $5\times10^{14}$ $M^{-1}$, at least $10^{15}$ $M^{-1}$, or at least $5\times10^{15}$ $M^{-1}$ as assessed using an assay described herein or known to one of skill in the art (e.g., a BIAcore assay).

In one embodiment, the invention provides methods for preventing, treating, or managing an RSV infection in a subject, the method comprising administering a pharmaceutically effective amount of at least one anti-F protein epitope or F peptide binder (e.g., antibodies or fragments thereof). In certain embodiments, a pharmaceutically effective amount reduces virus host cell fusion by at least 10%, or by at least 15%, or by at least 20%, or by at least 30%, or by at least 40%, or by at least 50%, or by at least 60%, or by at least 70%, or by at least 80%, or by at least 90%, or by at least 95%, or by at least 99%, or by at least 99.5%.

In another embodiment, the invention provides methods for preventing, treating, or managing a RSV infection in a subject, the method comprising administering a pharmaceutically effective amount of at least one F protein epitope or F peptide of the invention. In certain embodiments, a pharmaceutically effective amount reduces virus host cell fusion by at least 10%, or by at least 15%, or by at least 20%, or by at least 30%, or by at least 40%, or by at least 50%, or by at least 60%, or by at least 70%, or by at least 80%, or by at least 90%, or by at least 95%, or by at least 99%, or by at least 99.5%. In one embodiment, the F peptide mimics the F protein and binds to the natural receptor on host's cells and thus prevents RSV infection.

In one embodiment, the F peptides of the invention are at least 50%, or at least 60%, or at least 70%, or at least 80%, or at least 90%, or at least 95%, or at least 99%, or at least 99.5% identical to an F protein epitope of the RSV virus that causes the infection in the subject. In another embodiment, a derivative of an F peptide of the invention can be used to prevent viral fusion. Such derivatives include, but are not limited to, F peptides that have been modified (e.g., methylated, acetylated, carboxylated, glycosylated), substituted with non native amino acids, truncated so that stretches of amino acids are removed, or lengthened, so that single amino acids or stretches thereof have been added. In yet another embodiment, the F peptides are used to treat, manage, or prevent RSV infection. In still another embodiment, a combination of F peptides are administered to treat, manage, or prevent RSV infection.

DETAILED DESCRIPTION OF DRAWINGS

FIG. 1 shows the primary amino acid sequence of the RSV fusion (F) glycoprotein (SEQ ID No. 29). Underlined is the approximate A site within the F glycoprotein.

FIG. 2 shows SYNAGIS® and NUMAX™ MARMs in a portion of the RSV F protein antigenic A site sequence from amino acids #257 to #283. The amino acid changes at positions #258, #262, #268, #272, and #275 and #276 in the F protein antigenic A site are indicated. The ability of either SYNAGIS® or NUMAX™ to neutralize the F peptides with each single amino acid change is indicated "+" for maintenance of neutralizing ability and "−" for loss of ability as assessed by microneutralization assay.

Figure 5:
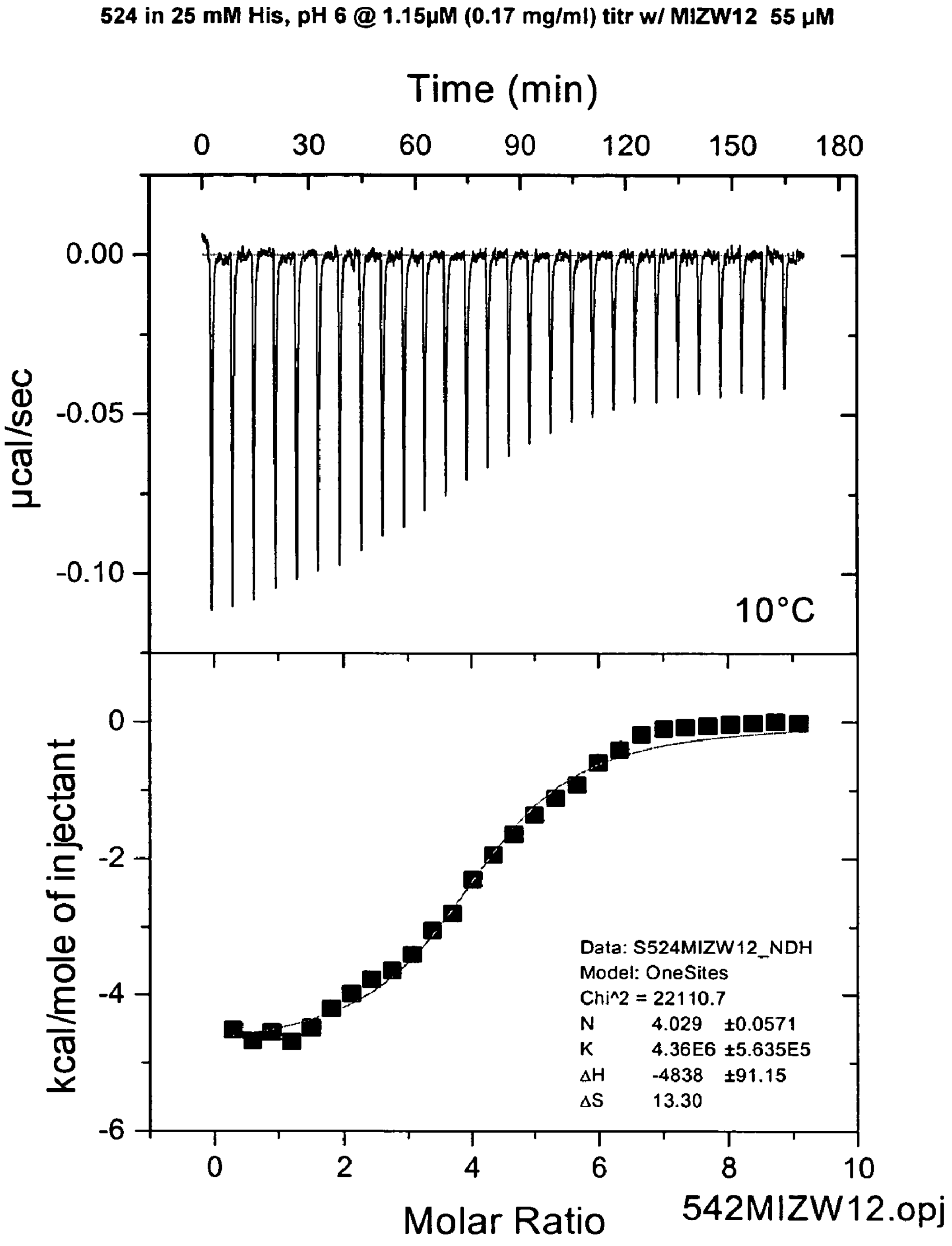

FIG. 5 graphically shows a binding titration of MEDI-524 with the F protein epitope (SEQ ID NO:1) using the ITC technique.

DEFINITIONS

The term "analog" as used herein refers to a polypeptide that possesses a similar or identical function as the F protein SEQ ID No.29 or a fragment thereof, but does not necessarily comprise a similar or identical amino acid sequence of the F protein. A polypeptide that has a similar amino acid sequence refers to a polypeptide that satisfies at least one of the following: (a) a polypeptide comprising an amino acid sequence that is at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or at least 99% identical to the amino acid sequence of SEQ ID NO: 29, or a fragment thereof; (b) a polypeptide encoded by a nucleotide sequence that hybridizes under stringent conditions to a nucleotide sequence encoding the amino acid sequence of SEQ ID NO: 29, or a fragment thereof of at least 5 amino acid residues, or at least 10 amino acid residues, or at least 15 amino acid residues, or at least 20 amino acid residues, or at least 25 amino acid residues; and (c) a polypeptide encoded by a nucleotide sequence that is at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or at least 99% identical to the nucleotide sequence encoding the amino acid sequence of SEQ ID NO: 29, or a fragment thereof.

The term "epitopes" as used herein refers to regions of an RSV F glycoprotein having antigenic or immunogenic activity in an animal, preferably a mammal, and most preferably in a human. An epitope having immunogenic activity is a fragment of a RSV polypeptide that elicits an antibody response in an animal. An epitope having antigenic activity is a fragment of a RSV polypeptide to which an antibody immunospecifically binds as determined by any method well known in the art, for example, by the immunoassays described herein. Antigenic epitopes need not necessarily be immunogenic.

A polypeptide with "similar structure" to an F protein epitope of the invention or fragment thereof described herein refers to a polypeptide that has a similar secondary, tertiary or quaternary structure to that of an F protein epitope of the invention or a fragment thereof described herein. The structure of a polypeptide can be determined by methods known to those skilled in the art, including but not limited to, X-ray crystallography, nuclear magnetic resonance, and crystallographic electron microscopy. Alternatively, the structure of a polypeptide can be predicted by methods known to those skilled in the art, including but not limited to, computer modeling by using, for example, an energy minimized molecular mechanics calculation, or building theoretical models of a binding site.

The term "derivative" as used herein refers to a peptide that comprises an F protein epitope of the invention or a fragment thereof, an anti-F peptide antibody or fragment thereof that has been altered by the introduction of amino acid residue substitutions, deletions or additions. The term "derivative" as used herein also refers to an F protein epitope or F peptide of the invention or a fragment thereof, an anti-F protein epitope antibody or an F peptide antibody or a fragment thereof that has been modified, e.g., by the covalent attachment of any type of molecule to the polypeptide. For example, but not by way of limitation, an F peptide of the invention or fragment thereof, an anti-F peptide antibody or fragment thereof may be modified, e.g., by glycosylation, acetylation, pegylation, phosphorylation, amidation, derivatization by known protecting/blocking groups, proteolytic cleavage, linkage to a cellular ligand or other protein, etc. A derivative of an F peptide of the invention or fragment thereof, an anti-F peptide antibody or fragment thereof may be modified by chemical modifications using techniques known to those of skill in the art, including, but not limited to specific chemical cleavage, acetylation, formylation, metabolic synthesis of tunicamycin, etc. Further, a derivative of an F peptide or fragment thereof, an anti-F peptide antibody or fragment thereof may contain one or more non-classical amino acids. A polypeptide derivative possesses a similar or identical function as an F peptide or fragment thereof, an anti-F peptide antibody or fragment thereof, described herein.

The term "effective neutralizing titer" as used herein refers to the amount of antibody which corresponds to the amount present in the serum of animals (human or cotton rat) that has been shown to be either clinically efficacious (in humans) or to reduce virus by at least 99% in, for example, cotton rats. The 99% reduction is defined by a specific challenge of, e.g., $10^3$ pfu, $10^4$ pfu, $10^5$ pfu, $10^6$ pfu, $10^7$ pfu, $10^8$ pfu, or $10^9$ pfu of RSV.

An "isolated" or "purified" polypeptide (e.g., an F peptide or fragment thereof, or an anti-F protein epitope antibody or anti-F peptide antibody or fragment thereof) is substantially free of cellular material or other contaminating proteins from the cell or tissue source from which the protein is derived, or substantially free of chemical precursors or other chemicals when chemically synthesized. The language "substantially free of cellular material" includes preparations of a polypeptide in which the polypeptide is separated from cellular components of the cells from which it is isolated or recombinantly produced. Thus, a polypeptide that is substantially free of cellular material includes preparations of a polypeptide having less than about 30%, or about 20%, or about 10%, or about 5%, or about 1% (by dry weight) of heterologous protein (also referred to herein as a "contaminating protein"). When the polypeptide is recombinantly produced, it is also preferably substantially free of culture medium, e.g., culture medium represents less than about 20%, or about 10%, or about 5%, or about 1% of the volume of the protein preparation. When the polypeptide is produced by chemical synthesis, it is preferably substantially free of chemical precursors or other chemicals, e.g., it is separated from chemical precursors or other chemicals that are involved in the synthesis of the protein. Accordingly such preparations of a polypeptide have less than about 30%, or about 20%, or about 10%, or about 5%, or about 1% (by dry weight) of chemical precursors or compounds other than the polypeptide(s) of interest. In a preferred embodiment, an F peptide, or fragment thereof, or an anti-F peptide antibody or fragment thereof, is isolated or purified.

An "isolated" nucleic acid molecule is one that is separated from other nucleic acid molecules that are present in the natural source of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. In a preferred embodiment, nucleic acid molecules encoding antibodies of the invention or fragments thereof are isolated or purified.

The term “fusion protein” as used herein refers to a polypeptide that comprises an amino acid sequence derived from an anti-F peptide binder (e.g., an antibody) or fragment thereof and an amino acid sequence of a heterologous polypeptide (e.g., a non-anti-RSV antigen antibody). Additionally, “fusion protein” refers to a heterologous peptide comprising the at least one F protein epitope and/or F peptide or fragment thereof and another polypeptide (e.g., an IgG Fc domain peptide or serum albumin).

The term “host cell” as used herein refers to the particular subject cell transfected with a nucleic acid molecule and the progeny or potential progeny of such a cell. Progeny of such a cell may not be identical to the parent cell transfected with the nucleic acid molecule due to mutations or environmental influences that may occur in succeeding generations or integration of the nucleic acid molecule into the host cell genome.

In certain embodiments of the invention, a “prophylactically effective serum titer” is the serum titer in a mammal, preferably a human, which reduces the incidence of a RSV infection in said mammal. Preferably, the prophylactically effective serum titer reduces the incidence of RSV infections in humans with the greatest probability of complications resulting from RSV infection (e.g., a human with cystic fibrosis, bronchopulmonary dysplasia, congenital heart disease, congenital immunodeficiency or acquired immunodeficiency, a human who has had a bone marrow transplant, a human infant, or an elderly human).

In certain embodiments of the invention, a “therapeutically effective serum titer” is the serum titer in a mammal, preferably a human that reduces the severity, the duration and/or the symptoms associated with a RSV infection in said mammal. Preferably, the therapeutically effective serum titer reduces the severity, the duration and/or the number symptoms associated with RSV infections in humans with the greatest probability of complications resulting from a RSV infection (e.g., a human with cystic fibrosis, bronchopulmonary dysplasia, congenital heart disease, congenital immunodeficiency or acquired immunodeficiency, a human who has had a bone marrow transplant, a human infant, or an elderly human). In certain other embodiments of the invention, a “therapeutically effective serum titer” is the serum titer in a cotton rat that results in an RSV titer 5 days after challenge with $10^5$ pfu that is at least 99% lower than the RSV titer 5 days after challenge with $10^5$ pfu of RSV in a cotton rat not administered an F protein epitope and/or an F peptide and/or an anti-F protein epitope antibody or an anti-F peptide antibody or fragment thereof.

The term “an F protein epitope” is any stretch of amino acids along the native RSV F protein (SEQ ID NO. 29) that can elicit an immune response. In addition, the term also encompasses any contiguous stretch of amino acids along the native RSV F protein to which an anti-RSV antibody can immunospecifically bind, wherein such an antibody is not SYNAGIS® or NUMAX™ or any other previously described antibody. The term also comprises any 24 contiguous stretch of amino acids within the antigenic A site of the native RSV F protein (SEQ ID NO. 29) that can elicit an immune response and/or to which an anti-RSV antibody can immunospecifically bind, herein such an antibody is not SYNAGIS® or NUMAX™ or any other previously described antibody. As a non-limiting example of such F protein epitopes, an F protein epitope may be exemplified by, but not limited to, the 24 amino acid sequence defined in SEQ ID NO.: 1.

The term “F peptides of the invention” refers to an RSV-F peptide and variants, derivatives or fragments thereof, to which anti-RSV antibodies of the invention SYNAGIS®NUMAX™ immunospecifically bind, and wherein these antibodies are not SYNAGIS® or NUMAX™. F peptides of the invention refers to analogs, derivatives and variants of SEQ ID NO.:29 and fragments thereof. Such F peptides also encompass peptides having at least 80% sequence identity to the 24 amino acid sequence defined in SEQ ID NO.: 1, calculated as discussed below. Such F peptides may also encompass peptides with the following structure:

$NSEL_{\alpha}SLI_{\beta}DMPIT_{\gamma}DQK_{\delta}LM_{\epsilon}NN$
(SEQ ID NO:34)

where α may be either a leucine or a serine; where β may be an asparagine, a histidine, an alanine, a serine, an arginine, an aspartie acid, a lysine, a tyrosine, or a glutamine; where γ may be an asparagine or an isoleucine; where δ may be a glutamic acid, a glutamine, an aspartic acid, a threonine, a methionine, a lysine, or a tyrosine; and where ϵ may be a seine, a glutamic acid, or a pherlylalanine. It is contemplated within the scope of the invention that an F peptide may be exemplified by, but not limited to, those listed in Table 1, as well as other variants being at least 80% identical to SEQ ID No:1.

TABLE 1

| | |
|---|---|
| SEQ ID No. 1 | NSELLSLINDMPITNDQKKLMSNN |
| SEQ ID No. 2 | NSELLSLINDMPITNDQKRLMSNN |
| SEQ ID No. 3 | NSELLSLINDMPITNDQKQLMSNN |
| SEQ ID No. 4 | NSELLSLINDMPITNDQKTLMSNN |
| SEQ ID No. 5 | NSELLSLINDMPITNDQKELMSNN |
| SEQ ID No. 6 | NSELLSLINDMPITNDQKDLMSNN |
| SEQ ID No. 7 | NSELLSLINDMPITNDQKMLMSNN |
| SEQ ID No. 8 | NSELLSLINDMPITNDQKHLMSNN |
| SEQ ID No. 9 | NSELLSLIQDMPITNDQKKLMSNN |
| SEQ ID No. 10 | NSELLSLIYDMPITNDQKKLMSNN |
| SEQ ID No. 11 | NSELLSLIKDMPITNDQKKLMSNN |
| SEQ ID No. 12 | NSELLSLIDDMPITNDQKKLMSNN |
| SEQ ID No. 13 | NSELLSLIHDMPITNDQKKLMSNN |
| SEQ ID No. 14 | NSELLSLIRDMPITNDQKKLMSNN |
| SEQ ID No. 15 | NSELLSLISDMPITNDQKKLMSNN |
| SEQ ID No. 16 | NSELLSLIADMPITNDQKKLMSNN |
| SEQ ID No. 17 | NSELSSLINDMPITNDQKKLMSNN |
| SEQ ID No. 18 | NSELLSLINDMPITNDQKYLMSNN |
| SEQ ID No. 19 | NSELLSLINDMPITIDQKKLMSNN |
| SEQ ID No. 20 | NSELLSLINDMPITNDQKNLMSNN |
| SEQ ID No. 21 | NSELLSLINDMPITNDQKKLMFNN |
| SEQ ID No. 22 | NSELLSLINDMPITNDQKKLMSEN |
| SEQ ID No. 23 | NSELLSLINDMPITNDQKKLMSYN |
| SEQ ID No. 27 | NSELLSLINDMPITNDQKKLMSNNC-$NH_2$ |
| SEQ ID No. 28 | NSELLSLINDMPITNDQKKLMSNN-$NH_2$ |

It is also contemplated that the term “F peptides of the invention” also refers to an RSV-F peptide and variants, derivatives or fragments thereof, to which the antibodies SYNAGIS® and/or NUMAX™ immunospecifically bind.

As used herein, the terms "antibody" and "antibodies" refer to monoclonal antibodies, multispecific antibodies, fully human antibodies, humanized antibodies, camelised antibodies, chimeric antibodies, CDR-grafted antibodies, single-chain Fvs (scFv), disulfide-linked Fvs (sdFv), Fab fragments, F (ab') fragments, anti-idiotypic (anti-Id) antibodies (including, e.g., anti-Id antibodies to antibodies of the invention) and other recombinant antibodies known to one skilled in the art and epitope-binding fragments of any of the above. In particular, antibodies include immunoglobulin molecules and immunologically active fragments of immunoglobulin molecules, i.e., molecules that contain an antigen binding site, these fragments may or may not be fused to another immunoglobulin domain including but not limited to, an Fc region or fragment thereof. The skilled artisan will further appreciate that other fusion products may be generated including but not limited to, scFv-Fc fusions, variable region (e.g., VL and VH)-Fc fusions and scFv-scFv-Fc fusions. Immunoglobulin molecules can be of any type (e.g., IgG, IgE, IgM, IgD, IgA and IgY), class (e.g., IgG1, IgG2, IgG3, IgG4, IgA1 and IgA2) or subclass.

The term "specifically bind to the F peptide of the invention" as used herein refers to peptides, polypeptides, proteins, fusion proteins, antibodies, aptamers, small molecules (generally considered less than 10 kD in size), and any fragments or derivatives of the foregoing, that specifically bind to an F peptide of the invention, or a fragment thereof.

A peptide, polypeptide, protein, fusion protein, antibody, aptamer, or small molecule that specifically binds to an F peptide or a fragment thereof or an F protein epitope may bind to other peptides, polypeptides, or proteins with lower affinity as determined by, e.g., immunoassays, BIAcore, or other assays known in the art. For instance, antibodies or fragments thereof that specifically bind to an F peptide or a fragment thereof or an F protein epitope may be cross-reactive with related antigens. Preferably, antibodies or fragments thereof that immunospecifically bind to a particular F peptide or an F protein epitope preferentially binds that F peptide or an F protein epitope over other antigens. However, the present invention specifically encompasses antibodies with multiple specificities (e.g., an antibody with specificity for two or more discrete antigens (reviewed in Cao et al., 2003, *Adv Drug Deliv Rev* 55:171; Hudson et al., 2003, *Nat Med* 1:129, incorporated herein by reference) in the definition of an antibody that "immunospecifically binds to an F peptide or an F protein epitope." For example, bispecific antibodies contain two different binding specificities fused together. In the simplest case a bispecific antibody would bind to two adjacent epitopes on a single target antigen, such an antibody would not cross-react with other antigens (as described supra). Alternatively, bispecific antibodies can bind to two different antigens, such an antibody specifically binds to two different molecules but not to other unrelated molecules. In addition, an antibody that specifically binds an F peptide or an F protein epitope may cross-react with related F peptides or F protein epitopes. Antibodies or fragments that specifically bind to an F peptide or an F protein epitope of the invention or fragment thereof may have cross-reactivity with other antigens. Preferably, antibodies or fragments thereof that specifically bind to an F peptide or an F protein epitope of the invention or fragment thereof does not cross-react with other antigens.

Antibodies or fragments that immunospecifically bind to an F peptide or an F protein epitope can be identified, for example, by immunoassays, BIAcore, or other techniques known to those of skill in the art. An antibody or fragment thereof binds specifically to an F peptide or a fragment thereof or an F protein epitope when it binds to an F peptide or a fragment thereof or an F protein epitope with higher affinity than to any cross-reactive antigen as determined using experimental techniques, such as radioimmunoassays (RIA) and enzyme-linked immunosorbent assays (ELISAs). See, e.g., Paul, ed., 1989, Fundamental Immunology Second Edition, Raven Press, New York at pages 332-336 for a discussion regarding antibody specificity.

To determine the "percent identity" of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions.times.100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, *Proc. Natl. Acad. Sci. U.S.A.* 87:2264-2268, modified as in Karlin and Altschul, 1993, *Proc. Natl. Acad. Sci. U.S.A.* 90:5873-5877. Such an algorithm is incorporated into the NBLAST and XBLAST programs of Altschul et al., 1990, *J. Mol. Biol.* 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score-50, wordlength=3 to obtain amino acid sequences homologous to a protein molecule of the present invention. To obtain gapped alignments for comparison purposes, Gapped BLAST can be utilized as described in Altschul et al., 1997, *Nucleic Acids Res.* 25:3389-3402. Alternatively, PSI-BLAST can be used to perform an iterated search that detects distant relationships between molecules (Id.). When utilizing BLAST, Gapped BLAST, and PSI-Blast programs, the default parameters of the respective programs (e.g., of XBLAST and NBLAST) can be used (see, e.g., http://www.ncbi.nlm.nih.gov). Another preferred, non-limiting example of a mathematical algorithm utilized for the comparison of sequences is the algorithm of Myers and Miller, 1988, *CABIOS* 4:11-17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

The term "effective amount" as used herein refers to the amount of a therapy (e.g., an antibody of the invention) which is sufficient to reduce and/or ameliorate the severity and/or duration of an upper and/or lower respiratory tract RSV infection, otitis media, and/or a symptom or respiratory condition relating thereto (including, but not limited to, asthma, wheezing, RAD, or a combination thereof), prevent the advancement or progression of the upper and/or lower respiratory tract RSV infection, otitis media and/or a symptom or respiratory condition relating thereto (e.g., prevent the progression of an upper respiratory tract RSV infection to a lower respiratory tract RSV infection), prevent the recurrence, development, or onset of an upper and/or lower respiratory tract RSV infection, otitis media, and/or a symptom or respiratory condition relating thereto (including, but not limited to, asthma, wheezing, RAD, or a combination thereof), and/or enhance/improve the prophylactic or therapeutic effect(s) of another therapy (e.g., a therapy other than an antibody of the invention). Non-limiting examples of effective amounts of an antibody of the invention are provided in Section 5.3, infra.

As used herein, the terms "treat," "treatment" and "treating" refer to the reduction or amelioration of the progression, severity, and/or duration of an upper and/or lower respiratory tract RSV infection, otitis media, or a symptom or respiratory condition related thereto (such as asthma, wheezing, RAD, or a combination thereof) resulting from the administration of one or more therapies (including, but not limited to, the administration of one or more prophylactic or therapeutic agents). In specific embodiments, such terms refer to the reduction or inhibition of the replication of RSV, the inhibition or reduction in the spread of RSV to other tissues or subjects (e.g., the spread to the lower respiratory tract), the inhibition or reduction of infection of a cell with a RSV, or the amelioration of one or more symptoms associated with an upper and/or lower respiratory tract RSV infection or otitis media.

As used herein, the terms "prevent," "preventing," and "prevention" refer to the prevention or inhibition of the development or onset of an upper and/or lower respiratory tract RSV infection, otitis media or a respiratory condition related thereto in a subject, the prevention or inhibition of the progression of an upper respiratory tract RSV infection to a lower respiratory tract RSV infection, otitis media or a respiratory condition related thereto resulting from the administration of a therapy (e.g., a prophylactic or therapeutic agent), the prevention of a symptom of an upper and/or lower tract RSV infection, otitis media or a respiratory condition related thereto, or the administration of a combination of therapies (e.g., a combination of prophylactic or therapeutic agents).

The term "upper and/or lower respiratory" tract refers to the major passages and structures of the upper and/or lower respiratory tract including the nose or nostrils, nasal cavity, mouth, throat (pharynx), and voice box (larynx).

The term "lower respiratory" tract refers to the major passages and structures of the lower respiratory tract including the windpipe (trachea) and the lungs, including the bronchi, bronchioles, and alveoli of the lungs.

The term "SYNAGIS®" is used to refer to a humanized RSV monoclonal antibody directed against the F glycoprotein of RSV, and is currently FDA-approved for the passive immunoprophylaxis of serious RSV disease in high-risk children. SYNAGIS® is also known by its generic name, palivizumab. SEQ ID Nos. 30 and 31 show the amino acid sequences of the (A) light chain variable region and (B) heavy chain variable region, respectively of a monoclonal antibody that binds to a RSV antigen. For reference purposes, this is the amino acid sequence of the SYNAGIS® antibody disclosed in Johnson et al., J. Infect. Dis. 176:1215-1224 (1997).

The term "NUMAX™" is used to refer to an enhanced potency RSV-specific monoclonal antibody derived by in vitro affinity maturation of the complementarity-determining regions of the heavy and light chains of palivizumab. NUMAX™ is also known by its generic name, motavizumab. SEQ ID No. 32 and 33 show the amino acid sequences of the (A) light chain variable region and (B) heavy chain variable region, respectively, of a monoclonal antibody that binds to a RSV antigen. For reference purposes, this is the amino acid sequence of the NUMAX® antibody disclosed in U.S. Pat. No. 6,818,216 and in Wu et al., J. Mol. Bio. 350(1):126-144 (2005).

DETAILED DESCIPTION OF THE INVENTION

The present invention provides F protein epitopes and F peptides that bind SYNAGIS® and/or NUMAX™. In one embodiment, F protein epitopes and/or F peptides competitively inhibit the binding of SYNAGIS® and/or NUMAX™ to RSV F protein. NUMAX™. In a specific embodiment, one or more F protein epitopes and/or F peptides will be administered to a mammal as a vaccine or antigenic formulation to create an immune response to protect said mammal from an RSV infection. In another embodiment, one or more F protein epitopes and/or F peptides will be administered to a mammal to prevent RSV infection by passive immunization. Without being bound by any particular theory or mechanism, it is contemplated that the F protein epitopes and/or F peptides may bind to the natural receptor of the RSV F protein and block binding thereby preventing F protein mediated fusion of RSV with the cell.

The present invention also provides molecules, e.g., antibodies that specifically bind to one or more F protein epitopes and/or F peptides (e.g., anti-F protein epitope antibodies and/or anti-F peptide antibodies). It is contemplated that said antibodies are not Synagis® (palivizumab) or Numax™ (motavizumab) or murine mAbs 47F and 7C2 (see, Arbiza J. et al., J. Gen. Virol., 73:2225-2234 (1992)). The present invention additionally provides methods of preventing, neutralizing, treating and ameliorating one or more symptoms associated with a RSV infection in a subject comprising administering to said subject one or more said anti-F protein epitope binders and/or anti-F peptide binders, e.g., antibodies which may then will neutralize an RSV virus. In one embodiment, anti-F protein epitope antibodies or F peptide antibodies have a high affinity and/or high avidity and/or have a serum half-life that has been optimized. The high affinity and/or high avidity of said antibodies of the invention enable the use of lower doses of said antibodies than previously thought to be effective for the prevention, neutralization, treatment and the amelioration of symptoms associated with RSV infection. The use of lower doses of antibodies which specifically bind to one or more RSV antigens (e.g., F protein epitopes and/or F peptides), reduces the likelihood of adverse effects, as well as providing a more effective prophylaxis. Further, the high affinity and/or high avidity of an anti-F protein epitope antibody or an anti-F peptide antibody of the invention enable less frequent administration of said antibodies than previously thought to be necessary for the prevention, neutralization, treatment and the amelioration of symptoms associated with RSV infection.

The present invention also provides methods of preventing, neutralizing, treating and ameliorating one or more symptoms associated with a RSV infection in a subject comprising administering to said subject one or more anti-F protein epitope binders and/or anti-F peptide binders, e.g., antibodies, said binders having a longer half-life in vivo than other previously known binders. In particular, the present invention provides for said antibodies which have a half-life in a subject, preferably a mammal and most preferably a human, of greater than 3 days, greater than 7 days, greater than 10 days, preferably greater than 15 days, greater than 25 days, greater than 30 days, greater than 35 days, greater than 40 days, greater than 45 days, greater than 2 months, greater than 3 months, greater than 4 months, or greater than 5 months. To prolong the serum circulation of antibodies (e.g., monoclonal antibodies, single chain antibodies and Fab fragments) in vivo, for example, inert polymer molecules such as high molecular weight polyethyleneglycol (PEG) can be attached to the antibodies with or without a multifunctional linker either through site-specific conjugation of the PEG to the N- or C-terminus of the antibodies or via epsilon-amino groups present on lysine residues. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Antibodies having an increased half-life in vivo can also be generated by introducing one or more amino acid modifications (i.e., substitutions, insertions or deletions) into an IgG constant domain, or FcRn binding fragment thereof (preferably a Fc or hinge-Fc domain fragment). See, e.g., International Publication Nos. WO 02/06919; WO 98/23289; and WO 97/34631; and U.S. Pat. No. 6,277,375; each of which is incorporated herein by reference in its entirety. Such half life extension can also be achieved by conjugation to albumin. The techniques are well-known in the art, see, e.g., International Publication Nos. WO 93/15199, WO 93/15200, and WO 01/77137; and European Patent No. EP 413,622, all of which are incorporated herein by reference.

The present invention also provides methods of preventing, neutralizing, treating and ameliorating one or more symptoms associated with a RSV infection in a subject comprising administering to said subject one or more F protein epitope and/or F peptides of the invention as a vaccine or antigenic formulation to generate an immune response to protect said subject from an RSV infection. The present invention also provides for methods of administering the F protein epitope and/or F peptide as a passive immunization therapy to prevent RSV infections.

The present invention further provides methods of administering to a subject one or more anti-F peptide binders. The present invention encompasses methods of delivering one or more anti-F peptide binders, wherein said binder is capable of neutralizing RSV. In particular, the invention encompasses pulmonary delivery of one or more F peptides of the invention and/or one or more anti-F peptide binders. In particular, the invention encompasses pulmonary or intranasal delivery of at least one F protein epitope or F peptide of the invention and/or one or more anti-F protein epitope or F peptide binder (e.g., antibodies). As an example, pulmonary administration can be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety. In one embodiment, an antibody of the invention or fragment thereof, or composition of the invention is administered using Alkermes AIR.™. pulmonary drug delivery technology (Alkermes, Inc., Cambridge, Mass.). Alternatively, methods of administering an antibody or fragment thereof, or pharmaceutical composition include, but are not limited to, parenteral administration (e.g., intradermal, intramuscular, intraperitoneal, intravenous and subcutaneous), epidural, and mucosal (e.g., intranasal and oral routes). In one embodiment, antibodies of the present invention or fragments thereof, or pharmaceutical compositions are administered intramuscularly, intravenously, or subcutaneously. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The present invention provides methods of achieving or inducing a serum titer of at least 1 μg/ml, or at least 2 μg/ml, or at least 5 μg/ml, or at least 6 μg/ml, or at least 10 μg/ml, or at least 15 μg/ml, or at least 20 μg/ml, or at least 25 μg/ml, or at least 30 μg/ml, or at least 40 μg/ml, or at least 50 μg/ml, or at least 75 μg/ml, or at least 100 μg/ml, or at least 125 μg/ml, or at least 150 μg/ml, or at least 175 μg/ml, or at least 200 μg/ml, or at least 225 μg/ml, or at least 250 μg/ml, or at least 275 μg/ml, or at least 300 μg/ml, or at least 325 μg/ml, or at least 350 μg/ml, or at least 375 μg/ml, or at least 400 μg/ml of an anti-F protein epitope antibody and/or anti-F peptide antibody, or fragment thereof, while reducing or avoiding adverse affects. Preferably the serum titers are achieved approximately 30 days after administration of a first dose of such an antibody (or an F protein epitope and/or F peptide of the invention) and without administration of any other doses of said antibodies or fragments thereof.

In a specific embodiment, a serum titer in a non-primate mammal of at least 40 μg/ml, preferably at least 80 μg/ml, or at least 100 μg/ml, or at least 120 μg/ml, or at least 150 μg/ml, or at least 200 μg/ml, or at least 250 μg/ml, or at least 300 μg/ml, of one or more anti-F protein epitope antibodies and/or anti-F peptide antibodies is achieved at least 1 day after administering a dose of less than 2.5 mg/kg, preferably less than 1 mg/kg, or less than 0.5 mg/kg of the anti-F protein epitope antibodies and/or anti-F peptide antibodies or fragments thereof to the non-primate mammal.

In another embodiment, a serum titer in a non-primate mammal of at least 150 μg/ml, preferably at least 200 μg/ml, or at least 250 μg/ml, or at least 300 μg/ml, or at least 350 μg/ml, or at least 400 μg/ml of one or more anti-F protein epitope antibodies and/or anti-F peptide antibodies, or fragments thereof, is achieved at least 1 day after administering a dose of approximately 5 mg/kg of the anti-F protein epitope antibodies and/or anti-F peptide antibodies or fragments thereof to the non-primate mammal.

In another embodiment, a serum titer in a primate of at least 40 μg/ml, preferably at least 80 μg/ml, or at least 100 μg/ml, or at least 120 μg/ml, or at least 150 μg/ml, or at least 200. μg/ml, or at least 250 μg/ml, or at least 300 μg/ml of one or more anti-F protein epitope antibodies and/or anti-F peptide antibodies or fragments thereof is achieved at least 30 days after administering a first dose of less than 5 mg/kg, preferably less than 3 mg/kg, or less than 1 mg/kg, or less than 0.5 mg/kg of the anti-F protein epitope antibodies and/or anti-F peptide antibodies or fragments thereof to the primate.

In yet another embodiment, a serum titer in a primate of at least 200 μg/ml, or at least 250 μg/ml, or at least 300 μg/ml, or at least 350 μg/ml, or at least 400 μg/ml of one or more anti-F protein epitope antibodies and/or anti-F peptide antibodies or fragments thereof is achieved at least 30 days after administering a first dose of approximately 15 mg/kg of the antibodies or fragments thereof to the primate. In accordance with these embodiments, the primate is preferably a human.

The present invention provides methods for preventing, treating, or ameliorating one or more symptoms associated with a RSV infection in a mammal, preferably a human, said methods comprising administering a dose to said mammal of a prophylactically or therapeutically effective amount of one or more F protein epitope and/or F peptide of the invention and/or anti-F protein epitope antibodies and/or anti-F peptide antibodies or fragments thereof.

The present invention provides methods for preventing, treating, or ameliorating one or more symptoms associated with a RSV infection in a mammal, preferably a human, said methods comprising administering a first dose into a mammal of a prophylactically or therapeutically effective amount of one or more F protein epitope and/or F peptide of the invention and then a second dose of one or more anti-F protein epitope antibodies and/or anti-F peptide antibodies, or fragments thereof. In another embodiment the present invention provides methods for preventing, treating, or ameliorating one or more symptoms associated with a RSV infection in into a mammal, preferably a human, said methods comprising administering a first dose into a mammal of a prophylactically or therapeutically effective amount one or more anti-F protein epitope antibodies and/or anti-F peptide antibodies or fragments thereof then a second dose of one or more F protein epitope and/or F peptides of the invention. In another embodiment the present invention provides methods for preventing, treating, or ameliorating one or more symptoms associated with a RSV infection in a mammal, preferably a human, said methods comprising administering a concurrent dosing into a mammal of a prophylactically or therapeutically effective amount one or more anti-F protein epitope antibodies and/or anti-F peptide antibodies or fragments thereof and one or more F protein epitope and/or F peptides of the invention. It is specifically contemplated that any of the above methods may also encompass the administration of antibodies that immunospecifically bind to an RSV epitope that is not the F protein epitope and/or F peptide of the invention.

In certain embodiments, the invention provides methods for preventing, treating, or managing a RSV infection in a subject, the method comprising administering a pharmaceutically effective amount of one or more F protein epitope and/or F peptides of the invention. In certain embodiments, a pharmaceutically effective amount reduces virus host cell fusion by at least 10%, or by at least 15%, or by at least 20%, or by at least 30%, or by at least 40%, or by at least 50%, or by at least 60%, or by at least 70%, or by at least 80%, or by at least 90%, or by at least 95%, or by at least 99%, or by at least 99.5%. In a specific embodiment, an F peptide mimics the F protein and binds to the natural receptor on host's cells and thus prevents RSV infection.

In other embodiments, an F peptide of the invention is at least 50%, or at least 60%, or at least 70%, or at least 80%, or at least 90%, or at least 95%, or at least 98%, or at least 99%, or at least 99.5% identical to the peptide of the virus that causes the infection in the subject. In certain embodiments, a derivative of an F peptide of the invention can be used to prevent viral fusion. Such derivatives include, but are not limited to, peptides that have been substituted with non-native amino acids, truncated so that stretches of amino acids are removed, or lengthened, so that single amino acids or stretches thereof have been added. In yet another embodiment, an F peptide of the invention is used to treat, manage, or prevent RSV infection. In an even further embodiment, a combination of the above-described F peptides is administered to treat, manage, or prevent RSV infection.

In certain embodiments, the invention provides methods for preventing, treating, or managing a RSV infection in a subject, the method comprising administering a pharmaceutically effective amount of one or more anti-F peptide binders. In certain embodiments, a pharmaceutically effective amount reduces virus host cell fusion by at least 10%, or by at least 15%, or by at least 20%, or by at least 30%, or by at least 40%, or by at least 50%, or by at least 60%, or by at least 70%, or by at least 80%, or by at least 90%, or by at least 95%, or by at least 99%, or by at least 99.5%.

In other specific embodiments, the invention provides methods for preventing, treating, or managing a RSV infection in a subject, the method comprising administering a pharmaceutically effective amount of one or more anti-F peptide antibodies. In certain embodiments, a pharmaceutically effective amount reduces virus host cell fusion by at least 10%, or by at least 15%, or by at least 20%, or by at least 30%, or by at least 40%, or by at least 50%, or by at least 60%, or by at least 70%, or by at least 80%, or by at least 90%, or by at least 95%, or by at least 99%, or by at least 99.5%.

Peptides of the Invention

In one embodiment of the invention, an F peptide of the invention or fragment thereof or pharmaceutical composition comprising said F peptide, is administered to a subject to treat, manage, or prevent RSV infection. In a preferred embodiment, said subject is a human. In a specific embodiment, the F peptide or fragment thereof or pharmaceutical composition comprising said F peptide is a vaccine or an immunogenic composition. Another embodiment includes the administration of an F peptide or fragment thereof or pharmaceutical composition comprising said F peptide as a passive immunotherapy. In certain embodiments, the invention provides methods for preventing, treating, or managing a RSV infection in a subject, the methods comprising administering a pharmaceutically effective amount of one or more F peptide of the invention. In other embodiments, a pharmaceutically effective amount reduces virus host cell fusion by at least 10%, or by at least 15%, or by at least 20%, or by at least 30%, or by at least 40%, or by at least 50%, or by at least 60%, or by at least 70%, or by at least 80%, or by at least 90%, or by at least 95%, or by at least 99%, or by at least 99.5%.

In certain embodiments, an F peptide of the invention is at least or at least 60%, or at least 70%, or at least 80%, or at least 90%, or at least 95%, or at least 98%, or at least 99%, or at least 99.5% identical to SEQ ID NO.: 1. The invention further provides polynucleotides comprising a nucleotide sequence encoding F peptide peptides of the invention.

In certain embodiments, a derivative of an F peptide of the invention can be used to prevent viral fusion. Such derivatives include, but are not limited to, peptides that have been substituted with non-native amino acids, truncated so that stretches of amino acids are removed, or lengthened so that single amino acids or stretches thereof have been added. The invention also encompasses any variants of an F peptide. Variants include but are not limited to substitution and/or by addition and/or deletion of one or more amino acids, provided that this modification does not impair the antigenic, immunogenic properties or binding capabilities of the polypeptide.

It is specifically contemplated that conservative amino acid substitutions may be made in an F peptide. It is well known in the art that "conservative amino acid substitution" refers to amino acid substitutions that substitute functionally equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide.

Substitutions that are charge neutral and which replace a residue with a smaller residue may also be considered "conservative substitutions" even if the residues are in different groups (e.g., replacement of phenylalanine with the smaller isoleucine). Families of amino acid residues having similar side chains have been defined in the art. Several families of conservative amino acid substitutions are shown in Table 2.

TABLE 2

Families of Conservative Amino Acid Substitutions

| Family | Amino Acids |
|---|---|
| non-polar | Trp, Phe, Met, Leu, Ile, Val, Ala, Pro |
| uncharged polar | Gly, Ser, Thr, Asn, Gln, Tyr, Cys |
| acidic/negatively charged | Asp, Glu |
| basic/positively charged | Arg, Lys, His |
| Beta-branched | Thr, Val, Ile |
| residues that influence chain orientation | Gly, Pro |
| aromatic | Trp, Tyr, Phe, His |

The term "conservative amino acid substitution" also refers to the use of amino acid analogs or variants. Guidance concerning how to make phenotypically silent amino acid substitutions is provided in Bowie et al., "Deciphering the Message in Protein Sequences: Tolerance to Amino Acid Substitutions," (1990, *Science* 247:1306-1310), incorporated herein by reference.

In other embodiments, variants of an F peptide are generated to improve certain characteristics including but not limited to, solubility, stability, pI, and serum half-life. For example, peptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. See Pinckard et al., *Clin. Exp. Immunol.* 2:331-340 (1967); Robbins et al., *Diabetes* 36: 838-845 (1987); Cleland et al., *Crit. Rev. Therapeutic Drug Carrier Systems* 10:307-377 (1993), each of which are incorporated herein by reference.

In a preferred embodiment, an F peptide of the invention is used to treat, manage, or prevent RSV infection. In another preferred embodiment, a combination of F peptides is administered to treat, manage, or prevent RSV infection. In still another preferred embodiment, a combination of one or more F peptides and/or one more anti-F peptide antibodies is administered to treat, manage, or prevent RSV infection. In a specific embodiment, doses of individual components are administered sequentially. In another specific embodiment, doses of individual components are administered concurrently.

Generation of an F Peptide

F peptides can be generated by numerous means including but not limited to, chemical synthesis and recombinant protein expression. Soluble peptides can be expressed and purified from a host cell. In one embodiment, synthetic recombinant DNAs are prepared that encode an F peptide of the invention.

In another embodiment, synthetic recombinant DNAs are prepared that additionally contain sequence tags useful in facilitating purification of an F peptide. In a preferred embodiment of the invention, the tag that facilitates purification of the F peptide does not interfere with its activity. In a specific embodiment, the tag amino acid sequence is a hexa-histidine peptide, such as the tag provided in a pQE vector (QIAGEN, Inc., 9259 Eton Avenue, Chatsworth, Calif., 91311). Other peptide tags useful for purification include, but are not limited to, the hemagglutinin "HA" tag, which corresponds to an epitope derived from the influenza hemagglutinin protein (Wilson et al., 1984, *Cell* 37:767) and the "flag" tag.

There are a number of different approaches that can be used to express and purify soluble peptides. The DNA sequence of an F peptide may be manipulated using methods well known in the art for the manipulation of nucleotide sequences, e.g., recombinant DNA techniques, (see, for example, the techniques described in *Current Protocols in Molecular Biology*, F. M. Ausubel et al., ed., John Wiley & Sons (Chichester, England, 1998); *Molecular Cloning: A Laboratory Manual,* 3nd Edition, J. Sambrook et al., ed., Cold Spring Harbor Laboratory Press (Cold Spring Harbor, N.Y., 2001), each of which are incorporated herein by reference). DNA vectors encoding an F peptide are prepared and subsequently transformed into an appropriate expression host cell, such as, e.g., *E. coli* strain BL21 (DE3), and the protein is expressed and purified using methods routine in the art. For example, expression of a gene encoding the peptide with a histidine tag can be induced from a pET vector using IPTG. Cells can then be lysed and the expressed peptide can be isolated after immobilization on a Ni-chelated Sepharose affinity column following elution with a counter charged species, for e.g., imidazole.

The invention also specifically encompasses fusion proteins comprising an F peptide. Polypeptides, proteins and fusion proteins can be produced by standard recombinant DNA techniques or by protein synthetic techniques, e.g., by use of a peptide synthesizer. For example, a nucleic acid molecule encoding a peptide, polypeptide, protein or a fusion protein can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, e.g., *Current Protocols in Molecular Biology*, Ausubel et al., eds., John Wiley & Sons, 1992). Moreover, a nucleic acid encoding a bioactive molecule can be cloned into an expression vector containing an F peptide such that the bioactive molecule is linked in-frame to the F protein epitope.

F protein epitopes according to the invention may be purified and isolated by methods known in the art. In particular, having identified the gene sequence, it will be possible to use recombinant techniques to express the genes in a suitable host. In addition, the peptides may be synthesized synthetically. Active fragments and related molecules can be identified and may be useful in therapy. For example, the peptides or their active fragments may be used as antigenic determinants in a vaccine, to elicit an immune response. They may also be used in the preparation of antibodies, for passive immunization, or diagnostic applications. Suitable antibodies include monoclonal antibodies, or fragments thereof, including single chain Fv fragments. Humanized antibodies are also within the scope of the invention. Methods for the preparation of antibodies will be apparent to those skilled in the art and are reviewed below.

The F protein epitopes of the invention can be coupled with a carrier that enhances isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin or bovine serum albumin (BSA), gelatin, or immunoglobulins; hydrophilic polymers such as polyvinylpyrrolidone; amino acids, such as glycine, glutamic acid, aspartic acid, or arginine, or ornithine, or cysteine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The present invention encompasses a fusion of an F peptide with another compound, such as a compound to increase the stability and/or solubility of the polypeptide (for example, polyethylene glycol), fusion of the peptide with additional amino acids, such as, for example, an IgG Fc fusion region peptide, serum albumin (preferably human serum albumin) or a fragment thereof, or leader or secretory sequence, or a sequence facilitating purification, or fusion of the peptide with another compound, such as albumin (including but not limited to recombinant albumin (see, e.g., U.S. Pat. No. 5,876,969, issued Mar. 2, 1999, EP Patent 0 413 622, and U.S. Pat. No. 5,766,883, issued Jun. 16, 1998, herein incorporated by reference in their entirety). Such variant peptides are deemed to be within the scope of those skilled in the art from the teachings herein.

Antibodies and Other Binders

It should be recognized that antibodies that specifically bind the F peptide are known in the art. For example, SYNAGIS® is a humanized monoclonal antibody presently used for the prevention of RSV infection in pediatric patients.

The invention encompasses novel antibodies, fragments and other biological or macromolecules which specifically bind to an F protein epitope of the invention (e.g., anti-F peptide antibodies). In certain embodiments, the invention provides methods for preventing, treating, or managing a RSV infection in a subject, the method comprising administering a pharmaceutically effective amount of an anti-F protein epitope binder, e.g., antibody, or fragment thereof. In certain embodiments, a pharmaceutically effective amount reduces virus host cell fusion by at least 10%, or by at least 15%, or by at least 20%, or by at least 30%, or by at least 40%, or by at least 50%, or by at least 60%, or by at least 70%, or by at least 80%, or by at least 90%, or by at least 95%, or by at least 99%, or by at least 99.5%.

The present invention further provides anti-F peptide antibodies or fragments thereof. Anti-F peptide antibodies of the invention include, but are not limited to, monoclonal antibodies, multispecific antibodies, human antibodies, humanized antibodies, chimeric antibodies, single-chain Fvs (scFv), single chain antibodies, Fab fragments, F (ab') fragments, disulfide-linked Fvs (sdFv), and anti-idiotypic (anti-Id) antibodies (including, e.g., anti-Id antibodies to antibodies of the invention), and epitope-binding fragments of any of the above. In particular, antibodies of the present invention include immunoglobulin molecules and immunologically active portions of immunoglobulin molecules, i.e., molecules that contain an antigen binding site that immunospecifically binds to a RSV antigen. The immunoglobulin molecules of the invention can be of any type (e.g., IgG, IgE, IgM, IgD, IgA and IgY), class (e.g., $IgG_1$, $IgG_2$, $IgG_3$, $IgG_4$, $IgA_1$ and IgA2) or subclass of immunoglobulin molecule.

The antibodies of the invention may be from any animal origin including birds and mammals (e.g., human, murine, donkey, sheep, rabbit, goat, guinea pig, camel, horse, or chicken). Preferably, the antibodies of the invention are human or humanized monoclonal antibodies. As used herein, "human" antibodies include antibodies having the amino acid sequence of a human immunoglobulin and include antibodies isolated from human immunoglobulin libraries or from mice that express antibodies from human genes.

Antibodies of the present invention can be prepared using a wide variety of techniques known in the art including the use of hybridoma, recombinant, and phage display technologies, or a combination thereof. For example, monoclonal antibodies can be produced using hybridoma techniques including those known in the art and taught, for example, in *Antibodies: A Laboratory Manual*, E. Harlow and D. Lane, ed., Cold Spring Harbor Laboratory Press (Cold Spring Harbor, N.Y., 1988); and Hammerling, et al., in: *Monoclonal Antibodies and T-Cell Hybridomas* 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice (or other mammals) can be immunized with an antigen of interest (e.g., an F protein epitope of the invention), and once an immune response is detected, e.g., antibodies specific for an F protein epitope of the invention are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. Additionally, a RIMMS (repetitive immunization, multiple sites) technique can be used to immunize an animal (Kilpatrick et al., 1997, *Hybridoma* 16:381-9, incorporated herein by reference in its entirety). Hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

For some uses, including in vivo use of antibodies in humans and in vitro detection assays, it may be preferable to use humanized antibodies or chimeric antibodies. Completely human antibodies and humanized antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International publication Nos. WO 98/46645, WO 98/50433, WO 98/24893, WO98/16654, WO 96/34096, WO 96/33735, and WO 91/10741; each of which is incorporated herein by reference in its entirety.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', $F(ab')_2$, Fv) in which all or substantially all of the CDR regions correspond to those of a non human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. Ordinarily, the antibody will contain both the light chain as well as at least the variable domain of a heavy chain. The antibody also may include the CH1, hinge, CH2, CH3, and CH4 regions of the heavy chain. The humanized antibody can be selected from any class of immuno-globulins, including IgM, IgG, IgD, IgA and IgE, and any isotype, including IgG1, IgG2, IgG3 and IgG4. Usually the constant domain is a complement fixing constant domain where it is desired that the humanized antibody exhibit cytotoxic activity, and the class is typically IgG1. Where such cytotoxic activity is not desirable, the constant domain may be of the IgG2 class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental framework and CDR sequences, more often 90%, and most preferably greater than 95%. A humanized antibody can be produced using variety of techniques known in the art, including but not limited to, CDR-grafting (see e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see e.g., European Patent Nos. EP 592,106 and EP 519,596; Padlan, 1991, Molecular Immunology 28(4/5): 489-498; Studnicka et al., 1994, Protein Engineering 7(6): 805-814; and Roguska et al., 1994, PNAS 91:969-973, each of which is incorporated herein by its entirety by reference), chain shuffling (see e.g., U.S. Pat. No. 5,565,332, which is incorporated herein in its entirety by reference), and techniques disclosed in, e.g., U.S. Pat. No. 6,407,213, U.S. Pat. No. 5,766,886, International Publication No. WO 9317105, Tan et al., 2002, *J. Immunol.* 169:1119-25, Caldas et al., 2000, *Protein Eng.* 13:353-60, Morea et al., 2000, *Methods* 20:267-79, Baca et al., 1997, *J. Biol. Chem.* 272:10678-84, Roguska et al., 1996, *Protein Eng.* 9:895-904, Couto et al., 1995, *Cancer Res.* 55:5973s-5977s, Couto et al., 1995, *Cancer Res.* 55:1717-22, Sandhu JS, 1994, *Gene* 150:409-10, and Pedersen et al., 1994, *J. Mol. Biol.* 235:959-73, each of which is incorporated herein in its entirety by reference. Often, framework residues in the framework regions will be substituted with the corresponding residue from the CDR donor antibody to alter, preferably improve, antigen binding. These framework substitutions are identified by methods well known in the art, e.g by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, *Nature* 332:323, which are incorporated herein by reference in their entireties.)

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring, which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, 1995, *Int. Rev. Immunol.* 13:65-93. For a detailed discussion of this technology for producing human antibodies and human monoclonal antibodies and protocols for producing such antibodies, see, e.g., International publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Human antibodies can also be derived from phage display of human antibody fragments. In phage display methods, functional antibody domains are displayed on the surface of phage particles, which carry the polynucleotide sequences encoding them. In particular, DNA sequences encoding $V_H$ and $V_L$ domains are amplified from animal cDNA libraries (e.g., human or murine cDNA libraries of lymphoid tissues). The DNA encoding the $V_H$ and $V_L$ domains are recombined together with an scFv linker by PCR and cloned into a phagemid vector (e.g., p CANTAB 6 or pComb 3 HSS). The vector is electroporated in *E. coli* and the *E. coli* is infected with helper phage. Phage used in these methods are typically filamentous phage including fd and M13 and the $V_H$ and $V_L$ domains are usually recombinantly fused to either the phage gene III or gene VIII. Phage expressing an antigen binding domain that binds to the antigen epitope of interest can be selected or identified with antigen, e.g., using labeled antigen or antigen bound or captured to a solid surface or bead. Examples of phage display methods that can be used to make the antibodies of the present invention include those disclosed in Brinkman et al., 1995, *J. Immunol. Methods* 182:41-50; Ames et al., 1995, *J. Immunol. Methods* 184:177; Kettleborough et al., 1994, *Eur. J. Immunol.* 24:952-958; Persic et al., 1997, *Gene* 187:9; Burton et al., 1994, *Advances in Immunology* 57:191-280; International Application No. PCT/GB91/01134; International Publication Nos. WO 90/02809, WO 91/10737, WO 92/01047, WO 92/18619, WO 93/1 1236, WO 95/15982, WO 95/20401, and WO97/13844; and U.S. Pat.

Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

In a preferred embodiment, after phage selection, the antibody coding regions from the phage are isolated and used to generate whole antibodies, including human antibodies as described in the above references. In another preferred embodiment the reconstituted antibody of the invention is expressed in any desired host, including bacteria, insect cells, plant cells, yeast, and in particular, mammalian cells (e.g., as described below). Techniques to recombinantly produce Fab, Fab' and $F(ab')_2$ fragments can also be employed using methods known in the art such as those disclosed in International Publication No. WO 92/22324; Mullinax et al., 1992, *BioTechniques* 12:864; Sawai et al., 1995, *AJRI* 34:26; and Better et al., 1988, *Science* 240:1041 (said references incorporated by reference in their entireties).

A chimeric antibody is a molecule in which different portions of the antibody are derived from different immunoglobulin molecules. Methods for producing chimeric antibodies are known in the art. See e.g., Morrison, 1985, *Science* 229:1202; Oi et al., 1986, *BioTechniques* 4:214; Gillies et al., 1989, *J. Immunol. Methods* 125:191-202; and U.S. Pat. Nos. 5,807,715, 4,816,567, 4,816,397, and 6,311,415, which are incorporated herein by reference in their entirety.

The antibodies of the present invention may be monospecific, bispecific, trispecific or of greater multispecificity. Multispecific antibodies may be specific the F peptide as well as for a heterologous epitope, such as a heterologous polypeptide or solid support material. See, e.g., PCT publications WO 93/17715, WO 92/08802, WO 91/00360, and WO 92/05793; Tutt, et al., J. Immunol. 147:60-69(1991); U.S. Pat. Nos. 4,474,893, 4,714,681, 4,925,648, 5,573,920, and 5,601,819; and Kostelny et al., J. Immunol. 148:1547-1553 (1992) which are incorporated herein by reference in their entirety.

Anti-F peptide antibodies of the present invention or fragments thereof may be characterized in a variety of ways. In particular, antibodies of the invention or fragments thereof may be assayed for the ability to specifically bind to the F peptide. Such an assay may be performed in solution (e.g., Houghten, 1992, *Bio/Techniques* 13:412-421), on beads (Lam, 1991, *Nature* 354:82-84), on chips (Fodor, 1993, *Nature* 364:555-556), on bacteria (U.S. Pat. No. 5,223,409), on spores (U.S. Pat. Nos. 5,571,698; 5,403,484; and 5,223,409), on plasmids (Cull et al., 1992, *Proc. Natl. Acad. Sci. USA* 89:1865-1869) or on phage (Scott and Smith, 1990, *Science* 249:386-390; Devlin, 1990, *Science* 249:404-406; Cwirla et al., 1990, *Proc. Natl. Acad. Sci. USA* 87:6378-6382; and Felici, 1991, *J. Mol. Biol.* 222:301-310) (each of these references is incorporated herein in its entirety by reference). Antibodies or fragments thereof that have been identified to specifically bind to the F peptide or a fragment thereof can then be assayed for their specificity and affinity for a RSV antigen.

The anti-F peptide antibodies of the invention or fragments thereof may be assayed for specific binding to F peptides and cross-reactivity with other antigens by any method known in the art. Immunoassays which can be used to analyze immunospecific binding and cross-reactivity include, but are not limited to, competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, *Current Protocols in Molecular Biology*, Vol. 1, John Wiley & Sons, Inc., New York, which is incorporated by reference herein in its entirety.

The invention provides polynucleotides comprising a nucleotide sequence encoding an anti-F peptide antibodyof the invention or a fragment thereof. The invention also encompasses polynucleotides that hybridize under high stringency, intermediate or lower stringency hybridization conditions, e.g., as defined supra, to polynucleotides that encode an antibody of the invention.

The present invention provides for anti-F peptide antibodies or fragments thereof that exhibit a high potency in an assay described herein. High potency and high affinity antibodies or fragments thereof can be produced by methods disclosed in copending U.S. patent application Ser. No. 09/796,848 and U.S. Pat. No. 6,656,467 (each of which are incorporated herein by reference) and methods described herein. For example, high potency antibodies can be produced by genetically engineering appropriate antibody gene sequences and expressing the antibody sequences in a suitable host. The antibodies produced can be screened to identify antibodies with, e.g., high $k_{on}$ values in a BIAcore assay.

The present invention also provides anti-F peptide antibodies or fragments thereof which immunospecifically bind to the F peptide and have an association rate constant or $k_{on}$ rate (antibody (Ab)+antigen (Ag) Ab-Ag) of at least $10^5$ $M^{-1}$ $s^{-1}$, or at least $5\times10^5$ $M^{-1}$ $s^{-1}$, at least $10^6 M^{-1}$ $s^{-1}$, or at least $5\times10^6 M^{-1}$ $s^{-1}$, or at least $10^7 M^{-1}$ $s^{-1}$, or at least $5\times10^7$ $M^{-1}$ $s^{-1}$, or at least $10^8$ $M^{-1}$ $s^{-1}$ as assessed using an described herein or known to one of skill in the art (e.g., a BIAcore assay).

The present invention provides anti-F peptide antibodies or fragments thereof that have a $k_{off}$ rate (antibody (Ab)+antigen (Ag) Ab-Ag) of less than $10^{-1}$ $s^{-1}$, or of less than $5\times10^{-1}$ $s^{-1}$, or of less than $10^{-2}$ $s^{-1}$, or of less than $5\times10^{-2}$ $s^{-1}$, or of less than $10^{-3}$ $s^{-1}$, or of less than $5\times10^{-3}$ $s^{-1}$, or of less than $10^{-4}$ $s^{-1}$, or of less than $5\times10^{-4}$ $s^{-1}$, or of less than $10^{-5}$ $s^{-1}$, or of less than $5\times10^{-5}$ $s^{-1}$, or of less than $10^{-6}$ $s^{-1}$, or of less than $5\times10^{-6}$ $s^{-1}$, or of less than $10^{-7}$ $s^{-1}$, or of less than $5\times10^{-7}$ $s^{-1}$, or of less than $10^{-8}$ $s^{-1}$, or of less than $5\times10^{-8}$ $s^{-1}$, or of less than $10^{-9}$ $s^{-1}$, or of less than 5.times.$10^{-9}$ $s^{-1}$, or of less than $10^{-10}$ $s^{-1}$ as assessed using an described herein or known to one of skill in the art (e.g., a BIAcore assay).

The present invention also provides anti-F peptide antibodies or fragments thereof that have an affinity constant or $K_a$ ($k_{on}/k_{off}$) of at least $10^2$ $M^{-1}$, or at least $5\times10^2$ $M^{-1}$, or at least $10^3$ $M^{-1}$, or at least $5\times10^3$ $M^{-1}$, or at least $10^4$ $M^{-1}$, or at least $5\times10^4$ $M^{-1}$, or at least $10^5$ $M^{-1}$, or at least $5\times10^5$ $M^{-1}$, or at least $10^6$ $M^{-1}$, or at least $5\times10^6$ $M^{-1}$, or at least $10^7$ $M^{-1}$, or at least $5\times10^7$ $M^{-1}$, or at least $10^8$ $M^{-1}$, or at least $5\times10^8$ $M^{-1}$, or at least $10^9$ $M^{-1}$, or at least $5\times10^9$ $M^{-1}$, or at least $10^{10}$ $M^{-1}$, or at least $5\times10^{10}$ $M^{-1}$, or at least $10^{11}$ $M^{-1}$, or at least $5\times10^{11}$ $M^{-1}$, or at least $10^{12}$ $M^{-1}$, or at least $5\times10^{12}$ $M^{-1}$, or at least $101^3$ $M^{-1}$, or at least $5\times10^{13}$ $M^{-1}$, or at least $10^{14}$ $M^{-1}$, or at least $5\times10^{14}$ $M^{-1}$, or at least $10^{15}$ $M^{-1}$, or at least $5\times10^{15}$ $M^{-1}$ as assessed using an described herein or known to one of skill in the art (e.g., a BIAcore assay).

The present invention provides anti-F peptide antibodies or fragments thereof that have a median effective concentration ($EC_{50}$) of less than 0.01 nM, or of less than 0.025 nM, or of less than 0.05 nM, or of less than 0.1 or of nM, less than 0.25 or of nM, less than 0.5 or of nM, less than 0.75 nM, or of less than 1 nM, or of less than 1.25 nM, or of less than 1.5 nM, or of less than 1.75 nM, or of less than 2 nM, in an in vitro microneutralization assay. In particular, the present invention provides compositions for use in the prevention, treatment or amelioration of one or more symptoms associated with a RSV infection, said compositions comprising one or more antibodies (e.g., anti-F peptide antibodies) or fragments thereof which immunospecifically bind to one or more RSV antigens and have an $EC_{50}$ of less than 0.01 nM, or of less than 0.025 nM, or of less than 0.05 nM, or of less than 0.1 nM, or of less than 0.25 nM, or of less than 0.5 nM, or of less than 0.75 nM, or of less than 1 nM, or of less than 1.25 nM, or of less than 1.5 nM, or of less than 1.75 nM, or of less than 2 nM, in an in vitro microneutralization assay.

The anti-F peptide antibodies of the invention include derivatives that are modified, i.e., by the covalent attachment of any type of molecule to the antibody such that covalent attachment. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The present invention also provides for F peptide binders, e.g., antibodies, or fragments thereof that have half-lives in a mammal, preferably a human, of greater than 15 days, preferably greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies of the present invention or fragments thereof in a mammal, preferably a human, results in a higher serum titer of said antibodies or antibody fragments in the mammal, and thus, reduces the frequency of the administration of said antibodies or antibody fragments and/or reduces the concentration of said antibodies or antibody fragments to be administered. Binders having increased in vivo half-lives can be generated by techniques known to those of skill in the art. For example, antibodies or fragments thereof with increased in vivo half-lives can be generated by modifying (e.g., substituting, deleting or adding) amino acid residues identified as involved in the interaction between the Fc domain and the FcRn receptor (see, e.g., PCT Publication No. WO 97/34631, which is incorporated herein by reference in its entirety). Such binders can be tested for binding activity to RSV antigens as well as for in vivo efficacy using methods known to those skilled in the art, for example, by immunoassays described herein.

Further, antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography. PEG-derivatizated antibodies or fragments thereof can be tested for binding activity to RSV antigens as well as for in vivo efficacy using methods known to those skilled in the art, for example, by immunoassays described herein.

The present invention also provides for fusion proteins comprising an antibody or fragment thereof that specifically binds the F peptide and a heterologous polypeptide. Preferably, the heterologous polypeptide that the antibody or antibody fragment is fused to be useful for targeting the antibody to respiratory epithelial cells.

The present invention also provides for panels of anti-F peptide antibodies or fragments thereof. In specific embodiments, the invention provides for panels of antibodies or fragments thereof having different affinities for an RSV antigen, different specificities for an F peptide, or different dissociation rates. The invention provides panels of at least 10, or preferably at least 25, or at least 50, or at least 75, or at least 100, or at least 125, or at least 150, or at least 175, or at least 200, or at least 250, or at least 300, or at least 350, or at least 400, or at least 450, or at least 500, or at least 550, or at least 600, or at least 650, or at least 700, or at least 750, or at least 800, or at least 850, or at least 900, or at least 950, or at least 1000 antibodies or fragments thereof. Panels of antibodies can be used, for example, in 96 well plates for assays such as ELISAs.

Anti-F protein epitopes antibodies of the present invention or fragments thereof may be used, for example, to purify, detect, and target RSV antigens, in both in vitro and in vivo diagnostic and therapeutic methods. For example, the antibodies or fragments have use in immunoassays for qualitatively and quantitatively measuring levels of the RSV in biological samples such as sputum. See, e.g., Harlow et al., *Antibodies: A Laboratory Manual*, (*Cold Spring Harbor Laboratory Press,* 2nd ed. 1988) (incorporated by reference herein in its entirety).

The present invention encompasses antibodies or fragments thereof recombinantly fused or chemically conjugated (including both covalently and non-covalently conjugations) to a heterologous polypeptide (or portion thereof, preferably at least 10, or at least 20, or at least 30, or at least 40, or at least 50, or at least 60, or at least 70, or at least 80, or at least 90, or at least 100 amino acids of the polypeptide) to generate fusion proteins. The fusion does not necessarily need to be direct, but may occur through linker sequences. For example, antibodies may be used to target heterologous polypeptides to particular cell types (e.g., respiratory epithelial cells), either in vitro or in vivo, by fusing or conjugating the antibodies to antibodies specific for particular cell surface receptors. Antibodies fused or conjugated to heterologous polypeptides may also be used in vitro immunoassays and purification methods using methods known in the art. See e.g., PCT publication WO 93/21232; EP 439,095; Naramura et al., 1994, *Immunol. Lett.* 39:91-99; U.S. Pat. No. 5,474,981; Gillies et al., 1992, *Proc. Natl. Acad. Sci. USA* 89:1428-1432 and Fell et al., 1991, *J. Immunol.* 146:2446-2452, which are incorporated by reference in their entireties.

The present invention further includes compositions comprising heterologous polypeptides fused or conjugated to anti-F protein epitopes antibody fragments. For example, the heterologous polypeptides may be fused or conjugated to a Fab fragment, Fd fragment, Fv fragment, $F(ab)_2$ fragment, or portion thereof. Methods for fusing or conjugating polypeptides to antibody portions are known in the art. See, e.g., U.S. Pat. Nos. 5,336,603, 5,622,929, 5,359,046, 5,349,053, 5,447,851, and 5,112,946; EP 307,434; EP 367,166; PCT publication Nos. WO 96/04388 and WO 91/06570; Ashkenazi et al., 1991, *Proc. Natl. Acad. Sci. USA* 88: 10535-10539; Zheng et al., 1995, *J. Immunol.* 154:5590-5600; and Vil et al., 1992,

*Proc. Natl. Acad. Sci. USA* 89:11337-11341 (said references incorporated by reference in their entireties).

Additional fusion proteins of the invention may be generated through the techniques of gene-shuffling, motif-shuffling, exon-shuffling, and/or codon-shuffling (collectively referred to as "DNA shuffling"). DNA shuffling may be employed to alter the activities of antibodies of the invention or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al., 1997, *Curr. Opinion Biotechnol.* 8:724-33; Harayama, 1998, *Trends Biotechnol.* 16(2):76-82; Hansson, et al., 1999, *J. Mol. Biol.* 287:265-76 and Lorenzo and Blasco, 1998, *Biotechniques* 24(2):308-13 (each of these patents and publications are hereby incorporated by reference in its entirety). In one embodiment, antibodies or fragments thereof, or the encoded antibodies or fragments thereof, may be altered by being subjected to random mutagenesis by error-prone PCR, random nucleotide insertion or other methods prior to recombination. In another embodiment, one or more portions of a polynucleotide encoding an antibody or antibody fragment, which portions immunospecifically bind to a RSV antigen may be recombined with one or more components, motifs, sections, parts, domains, fragments, etc. of one or more heterologous molecules.

Moreover, the anti-F peptide antibodies of the present invention or fragments thereof can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, *Proc. Natl. Acad. Sci. USA* 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, *Cell* 37:767) and the "flag" tag.

The present invention further encompasses anti-F peptide binders e.g., antibodies, or fragments thereof conjugated to a diagnostic or therapeutic agent. The anti-F peptide antibodies can be used diagnostically to, for example, monitor the development or progression of a RSV infection as part of a clinical testing procedure to, e.g., determine the efficacy of a given treatment regimen. Detection can be facilitated by coupling the antibody or fragment thereof to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 (incorporated herein by reference) for metal ions that can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include $^{125}I$, $^{131}I$, $^{111}In$ or $^{99}Tc$.

A F protein epitope binder or fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

Further, F protein epitope binder or fragment thereof may be conjugated to a therapeutic agent or drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, α-interferon, β-interferon, nerve growth factor, platelet derived growth factor, tissue plasminogen activator, an apoptotic agent, e.g., TNF-α, TNF-β, AIM I (see, International Publication No. WO 97/33899), AIM II (see, International Publication No. WO 97/34911), Fas Ligand (Takahashi et al., 1994, *J. Immunol.,* 6:1567-1574), and VEGI (see, International Publication No. WO 99/23105) 13 (each of these patents and publications are hereby incorporated by reference in its entirety), a thrombotic agent or an anti-angiogenic agent, e.g., angiostatin or endostatin; or, a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF")), or a growth factor (e.g., growth hormone ("GH")).

Techniques for conjugating such therapeutic moieties to antibodies are well known, see, e.g., Amon et al., "Monoclonal Antibodies For Immunotargeting Of Drugs In Cancer Therapy", in *Monoclonal Antibodies And Cancer Therapy*, Reisfeld et al. (eds.), pp. 243-56 (Alan R. Liss, Inc. 1985); Hellstrom et al., "Antibodies For Drug Delivery", in *Controlled Drug Delivery* (2nd Ed.), Robinson et al. (eds.), pp. 623-53 (Marcel Dekker, Inc. 1987); Thorpe, "Antibody Carriers Of Cytotoxic Agents In Cancer Therapy: A Review", in *Monoclonal Antibodies '84: Biological And Clinical Applications*, Pinchera et al. (eds.), pp. 475-506 (1985); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), pp. 303-16 (Academic Press 1985), and Thorpe et al., 1982, *Immunol. Rev.* 62:119-5813 (each of these publications are hereby incorporated by reference in their entirety).

An antibody or fragment thereof, with or without a therapeutic moiety conjugated to it, administered alone or in combination with cytotoxic factor(s) and/or cytokine(s) can be used as a therapeutic. Alternatively, an antibody can be conjugated to a second antibody to form an antibody heteroconjugate as described by Segal in U.S. Pat. No. 4,676,980, which is incorporated herein by reference in its entirety. Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

In one embodiment, the invention is directed to aptamers of an F protein epitope of the invention (e.g., aptamers of F protein epitope of the invention). As is known in the art, aptamers are macromolecules composed of nucleic acid (e.g., RNA, DNA) that bind tightly to a specific molecular target (e.g., an F protein epitope of the invention and the natural F protein receptor). A particular aptamer may be described by a linear nucleotide sequence and an aptamer is typically about 15-60 nucleotides in length. The chain of nucleotides in an aptamer form intramolecular interactions that fold the molecule into a complex three-dimensional shape, and this three-dimensional shape allows the aptamer to bind tightly to the surface of its target molecule. Given the extraordinary diversity of molecular shapes that exist within the universe of all possible nucleotide sequences, aptamers may be obtained for a wide array of molecular targets, including proteins and small molecules. In addition to high specificity, aptamers have very high affinities for their targets (e.g., affinities in the picomolar to low nanomolar range for proteins). Aptamers are chemically stable and can be boiled or frozen without loss of activity. Because they are synthetic molecules, they are amenable to a variety of modifications, which can optimize their function for particular applications. For in vivo applications, aptamers can be modified to dramatically reduce their sensitivity to degradation by enzymes in the blood. In addition, modification of aptamers can also be used to alter their biodistribution or plasma residence time.

Selection of aptamers that can bind an F protein epitope of the invention and/or a natural F protein receptor can be achieved through methods known in the art. For example, aptamers can be selected using the SELEX (Systematic Evolution of Ligands by Exponential Enrichment) method (Tuerk, C., and Gold, L., *Science* 249:505-510 (1990)). In the SELEX method, a large library of nucleic acid molecules (e.g., $10^{15}$ different molecules) is produced and/or screened with the target molecule (e.g., an F protein epitope of the invention and/or a natural F protein receptor). The target molecule is allowed to incubate with the library of nucleotide sequences for a period of time. Several methods can then be used to physically isolate the aptamer target molecules from the unbound molecules in the mixture and the unbound molecules can be discarded. The aptamers with the highest affinity for the target molecule can then be purified away from the target molecule and amplified enzymatically to produce a new library of molecules that is substantially enriched for aptamers that can bind the target molecule. The enriched library can then be used to initiate a new cycle of selection, partitioning, and amplification. After 5-15 cycles of this selection, partitioning and amplification process, the library is reduced to a small number of aptamers that bind tightly to the target molecule. Individual molecules in the mixture can then be isolated, their nucleotide sequences determined, and their properties with respect to binding affinity and specificity measured and compared. Isolated aptamers can then be further refined to eliminate any nucleotides that do not contribute to target binding and/or aptamer structure (i.e., aptamers truncated to their core binding domain). See Jayasena, S. D. *Clin. Chem.* 45:1628-1650 (1999) for review of aptamer technology; the entire teachings of which are incorporated herein by reference).

In particular embodiments, the aptamers of the invention have the binding specificity and/or functional activity described herein for the anti-F peptide antibodies of the invention. Thus, for example, in certain embodiments, the present invention is drawn to aptamers that have the same or similar binding specificity as described herein for the anti-F peptide antibodies of the invention (e.g., binding specificity for an F protein epitope of the invention). In particular embodiments, the aptamers of the invention can bind to an F protein epitope of the invention and inhibit one or more functions of an F protein epitope of the invention. As described herein, function of an F protein epitope of the invention include but are not limited to, promoting viral-cell fusion, promoting cell-cell fusion leading to syncytia formation, binding to its natural receptor.

In another embodiment, the aptamers of the invention are molecular mimics of an F protein epitope, referred to herein as "aptamer F protein epitope mimic". In a specific embodiment, an aptamer F protein epitope mimic will be recognized by an anti-F peptide antibodyas described herein. Without wishing to be bound by theory or mechanism, it anticipated that an aptamer F protein epitope mimic could bind to the natural receptor of the RSV F protein and block binding of the RSV associated F protein thus, preventing F protein mediated fusion of RSV with the cell. In a particular embodiment, the aptamer F protein epitope mimic of the invention can inhibit one or more functions of an F protein epitope of the invention (supra).

Prophylactic and Therapeutic Uses of F Peptide Binders, e.g., Antibodies

One or more anti-F peptide binders of the present invention or fragments thereof may be used locally or systemically in the body as a therapeutic. The anti-F peptide binders of this invention or fragments thereof may also be advantageously utilized in combination with other monoclonal or chimeric antibodies, or with lymphokines or hematopoietic growth factors (such as, e.g., IL-2, IL-3 and IL-7), which, for example, serve to increase the number or activity of effector cells which interact with the antibodies. The anti-F peptide binders of this invention or fragments thereof may also be advantageously utilized in combination with one or more drugs used to treat RSV infection such as, for example antiviral agents. Binders of the invention or fragments may be used in combination with one or more of the following drugs: NIH-351 (Gemini Technologies), recombinant RSV vaccine (MedImmune Vaccines), RSVf-2 (Intracel), F-50042 (Pierre Fabre), T-786 (Trimeris), VP-36676 (ViroPharma), RFI-641 (American Home Products), VP-14637 (ViroPharma), PFP-1 and PFP-2 (American Home Products), RSV vaccine (Avant Immunotherapeutics), and F-50077 (Pierre Fabre).

The anti-F peptide antibodies of the invention may be administered alone or in combination with other types of treatments (e.g., hormonal therapy, immunotherapy, and anti-inflammatory agents). Generally, administration of products of a species origin or species reactivity (in the case of antibodies) that is the same species as that of the patient is preferred. Thus, in a preferred embodiment, human or humanized antibodies, fragments derivatives, analogs, or nucleic acids, are administered to a human patient for therapy or prophylaxis.

In one embodiment, therapeutic or pharmaceutical compositions comprising anti-F peptide binders of the invention or fragments thereof are administered to a mammal, preferably a human, to treat, prevent or ameliorate one or more symptoms associated with RSV infection. In another embodiment, therapeutic or pharmaceutical compositions comprising an anti-F peptide binders or fragments thereof are administered to a human with cystic fibrosis, bronchopulmonary dysplasia, congenital heart disease, congenital immunodeficiency or acquired immunodeficiency, or to a human who has had a bone marrow transplant to treat, prevent or ameliorate one or more symptoms associated with RSV infection. In another embodiment, therapeutic or pharmaceutical compositions comprising F peptide binders of the invention or fragments thereof are administered to a human infant, preferably a human infant born prematurely or a human infant at risk of hospitalization for RSV infection to treat, prevent or ameliorate one or more symptoms associated with RSV infection. In yet another embodiment, therapeutic or pharmaceutical compositions comprising F peptide binders of the invention or fragments thereof are administered to the elderly or people in group homes (e.g., nursing homes or rehabilitation centers).

Otitis media is an infection or inflammation of the middle ear. This inflammation often begins when infections that cause sore throats, colds, or other respiratory or breathing problems spread to the middle ear. These can be viral or bacterial infections. RSV is the principal virus that has been correlated with otitis media. Seventy-five percent of children experience at least one episode of otitis media by their third birthday. Almost half of these children will have three or more ear infections during their first 3 years. It is estimated that medical costs and lost wages because of otitis media amount to $5 billion a year in the United States (Gates GA, 1996, Cost-effectiveness considerations in otitis media treatment; Otolaryngol Head Neck Sur. 114 (4): 525-530). Although otitis media is primarily a disease of infants and young children, it can also affect adults.

Otitis media not only causes severe pain but may result in serious complications if it is not treated. An untreated infection can travel from the middle ear to the nearby parts of the head, including the brain. Although the hearing loss caused by otitis media is usually temporary, untreated otitis media may lead to permanent hearing impairment. Persistent fluid in the middle ear and chronic otitis media can reduce a child's hearing at a time that is critical for speech and language development. Children who have early hearing impairment from frequent ear infections are likely to have speech and language disabilities.

Although many physicians recommend the use of antibiotics for the treatment of ear infections, antibiotic resistance has become an important problem in effective treatment of the disease. Further, new therapies are needed to prevent or treat viral infections that are associated with otitis media, particularly RSV.

About 12 million people in the U.S. have asthma and it is the leading cause of hospitalization for children. *The Merck Manual of Diagnosis and Therapy* (17th ed., 1999). Asthma is an inflammatory disease of the lung that is characterized by airway hyperresponsiveness ("AHR"), bronchoconstriction (i.e., wheezing), eosinophilic inflammation, mucus hypersecretion, subepithelial fibrosis, and elevated IgE levels. Asthmatic attacks can be triggered by environmental triggers (e.g. acarids, insects, animals (e.g., cats, dogs, rabbits, mice, rats, hamsters, guinea pigs, mice, rats, and birds), fungi, air pollutants (e.g., tobacco smoke), irritant gases, fumes, vapors, aerosols, chemicals, or pollen), exercise, or cold air. The cause(s) of asthma is unknown. However, it has been speculated that family history of asthma (London et al., 2001, Epidemiology 12(5):577-83), early exposure to allergens, such as dust mites, tobacco smoke, and cockroaches (Melen et al., 2001, 56(7):646-52), and respiratory infections (Wenzel et al., 2002, Am J Med, 112(8):672-33 and Lin et al., 2001, J Microbiol Immuno Infect, 34(4):259-64), such as RSV, may increase the risk of developing asthma. A review of asthma, including risk factors, animal models, and inflammatory markers can be found in O'Byme and Postma (1999), Am. J. Crit. Care. Med. 159:S41-S66, which is incorporated herein by reference in its entirety.

Current therapies are mainly aimed at managing asthma and include the administration of β-adrenergic drugs (e.g. epinephrine and isoproterenol), theophylline, anticholinergic drugs (e.g., atropine and ipratorpium bromide), corticosteroids, and leukotriene inhibitors. These therapies are associated with side effects such as drug interactions, dry mouth, blurred vision, growth suppression in children, and osteoporosis in menopausal women. Cromolyn and nedocromil are administered prophylatically to inhibit mediator release from inflammatory cells, reduce airway hyperresponsiveness, and block responses to allergens. However, there are no current therapies available that prevent the development of asthma in subjects at increased risk of developing asthma. Thus, new therapies with fewer side effects and better prophylactic and/or therapeutic efficacy are needed for asthma.

Reactive airway disease is a broader (and often times synonymous) characterization for asthma-like symptoms, and is generally characterized by chronic cough, sputum production, wheezing or dyspenea. Wheezing (also known as sibilant rhonchi) is generally characterized by a noise made by air flowing through narrowed breathing tubes, especially the smaller, tight airways located deep within the lung. It is a common symptom of RSV infection, and secondary RSV conditions such as asthma and brochiolitis. The clinical importance of wheezing is that it is an indicator of airway narrowing, and it may indicate difficulty breathing. Wheezing is most obvious when exhaling (breathing out), but may be present during either inspiration (breathing in) or exhalation. Wheezing most often comes from the small bronchial tubes (breathing tubes deep in the chest), but it may originate if larger airways are obstructed.

Citation or discussion of a reference herein shall not be construed as an admission that such is prior art to the present invention.

Biological Assays

The tests set forth below can be used to determine the effectiveness of an F peptide and its derivatives in preventing the fusion of RSV with a cell. The tests set forth below can also be used to determine the effectiveness of an anti-F peptide antibody in preventing the fusion of RSV with a cell. These methods and others, can be used to determine which F peptides, or anti-F peptide binders, e.g., antibodies, are best suited for treating, preventing, or managing and RSV infection in a subject.

Cell based assays used to determine the ability of a molecule (e.g., F peptide) to inhibit viral fusion have been described (see, for example Mufson et al., 1985, *J Gen Virol* 66:2111-2124, which is incorporated herein by reference in its entirety). Briefly upon infection of a host cell with RSV, the cells are incubated with an F protein epitope or anti-F peptide antibodypreparation and scored for fusion after incubation for an appropriate period of time. Cells are subsequently stained for synctium/polykaryon formation in order to determine whether viral-cell fusion was successful. Any cell that can be infected with RSV can be used in the assay, including, but not limited to, tMK, Hep2, and Vero cells. In a specific embodiment, the type of cells that are used are Hep2 cells.

Neutralization assays have also been described (see, for example, Beller et al., 1989, *J Virol* 63: 2941-2950, which is incorporated herein by reference in its entirety). Briefly RSV is incubated in the presence of serial dilutions of the agent(s) to be tested (e.g., F peptide) for an appropriate period of time. The mixtures of virus-agent(s) are then transferred to cell monolayers and incubated for an appropriate period of time. Cells are subsequently examined microscopically for cytopathology. Microscopic observations can be confirmed by staining with a glutaraldehyde-crystal violet solution. Neutralization can be expressed as the reciprocal of the highest agent dilution which inhibited more then 95% of the viral cytopathic effect present in the control sample (RSV and cells alone)

ELISA assays comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1. The binding affinity of an antibody to an antigen and the off-rate of an antibody-antigen interaction can be determined by competitive binding assays. One example of a competitive binding assay is a radioimmunoassay comprising the incubation of labeled antigen (e.g., $^3H$ or $^{125}I$) with the antibody of interest in the presence of increasing amounts of unlabeled antigen, and the detection of the antibody bound to the labeled antigen. The affinity of the antibody of the present invention for a RSV antigen and the binding off-rates can be determined from the data by scatchard plot analysis. Competition with a second antibody can also be determined using radioimmunoassays. In this case, a RSV antigen is incubated with an antibody of the present invention conjugated to a labeled compound (e.g., $^3H$ or $^{125}I$) in the presence of increasing amounts of an unlabeled second antibody. In a preferred embodiment, BIAcore kinetic analysis is used to determine the binding on and off rates of antibodies to a RSV antigen. BIAcore kinetic analysis comprises analyzing the binding and dissociation of a RSV antigen from chips with immobilized antibodies on their surface.

BIAcore analysis can measure the kinetic interactions of anti-RSV antibodies with RSV F peptides by surface plasmon resonance using a BIAcore 1000, 2000, or 3000 instrument (Biacore, Uppsala, Sweden). Purified recombinant, C-terminally truncated F protein was covalently coupled to a (1-ethyl-3-[3-dimethylaminopropyl]carbodiimide hydrochloride)/N-hydroxysuccinimide-activated CM5 sensor chip at a low protein density (see Johnsson et al. (1991) *Anal. Biochem.* 198, 268-277). The unreacted active ester groups were blocked with 1 M ethanolamine. For use as a reference, when the BIAcore 2000 or 3000 instrument was used, a blank surface, containing no antigen, was prepared under identical immobilization conditions. To minimize binding variations caused by different lots of F proteins, most of the antibodies were measured against the same lot of F protein. In several cases when different lots of F proteins were used, their binding to an anti-RSV antibody was used as a reference to make sure that these lots had similar binding characteristics to the lot that is used mainly. A serial 2-fold dilution series of purified antibodies, ranging from 0.2 to 100 nm in HBS/Tween 20 buffer (BIAcore), was injected over the F-protein and reference cell surfaces, which were connected in series. In each measurement, the residual antibody was removed from the sensor chip by a brief pulse of 100 mM HCl. The binding curves were globally fitted to a 1:1 Langmuir binding model using the BIAevaluation program. This algorithm calculates both $k_{on}$ and $k_{off}$. The apparent equilibrium dissociation constant, $K_d$, was deduced as the ratio of the two rate constants, $k_{off}/k_{on}$.

Isothermal Titration Calorimetry assays (ITC) have been described (see, for example, Heerklotz H et al., *Biophysical Journal*, May 1999). Molecular interactions are defined by stoichiometry and a few thermodynamic parameters. All binding reactions are associated with the absorption or generation of heat. Therefore calorimetry is emerging as a premier tool for the characterisation of interactions of biological macromolecules. ITC is the only method that measures equilibrium constants, enthalpy and entropy in one single experiment. If the experiment is performed at different temperatures the important parameter, the heat capacity change, can be determined. ITC has become a standard method for investigating the binding of ligands to receptor molecules. Accordingly, ligands are mixed with receptors, and the subsequent heats of incorporation (or binding) are measured.

With respect to the F peptide and the anti-F protein binders, the invention further encompasses novel modes of administration, doses, dosing and uses based, in part, upon their unique therapeutic profiles and potency.

The preparation of vaccines or immunogenic compositions based on the F peptide or anti-F protein binders, e.g., antibodies will be known to those skilled in the art. Vaccines or immunogenic compositions can be formulated with suitable carriers or adjuvants, e.g. alum, as necessary or desired, to provide effective immunization against infection. The preparation of vaccine formulations will be apparent to the skilled person.

More generally, and as is well known to those skilled in the art, a suitable amount of an active component of the invention can be selected, for therapeutic use, as can suitable carriers or excipients, and routes of administration. These factors would be chosen or determined according to known criteria such as the nature/severity of the condition to be treated, the type and/or health of the subject etc.

In a separate embodiment, the products of the invention may be used in screening assays for the identification of potential antimicrobial drugs (for example, antibodies, fusion proteins, small molecules etc.) or for the detection of virulence. Routine screening assays are known to those skilled in the art and can be adapted using the products of the invention in the appropriate way. For example, the products of the invention may be used as the target for a potential drug, with the ability of the drug to inactivate or bind to the target indicating its potential antiviral activity.

Another embodiment of the invention includes the use of an F protein epitope, F peptide or F peptide or F protein epitope binder in an in-vitro diagnostic kit to detect the infection in an animal, preferably a human, by RSV. In one embodiment, a kit comprises an antibody of the invention, preferably a purified antibody, in one or more containers. In a specific embodiment, the kits of the present invention contain a substantially isolated RSV antigen as a control. Preferably, the kits of the present invention further comprise a control antibody which does not react with the RSV antigen. In another specific embodiment, the kits of the present invention contain a means for detecting the binding of an antibody to a RSV antigen (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized RSV antigen. The RSV antigen provided in the kit may also be attached to a solid support. In a more specific embodiment the detecting means of the above described kit includes a solid support to which RSV antigen is attached. Such a kit may also include a non-attached reporter-labeled anti-human antibody. In this embodiment, binding of the antibody to the RSV antigen can be detected by binding of the said reporter-labeled antibody.

Methods of Administration

The invention provides methods of treatment, prophylaxis, and amelioration of one or more symptoms associated with RSV infection by administrating to a subject an F protein epitope of the invention, or a composition (e.g., pharmaceutical composition) comprising said peptide, or an effective amount of an anti-F protein epitope binder or fragment thereof, or a composition (e.g., pharmaceutical composition) comprising an anti-F protein epitope binder or fragment thereof. In a preferred aspect, the F protein epitope of the invention or the anti-F protein epitope binder or fragment thereof is substantially purified (i.e., substantially free from substances that limit its effect or produce undesired side-effects). The subject is preferably a mammal such as non-primate (e.g., cows, pigs, horses, cats, dogs, rats etc.) and a primate (e.g., monkey such as a cynomolgous monkey and a human). In a preferred embodiment, the subject is a human. In another preferred embodiment, the subject is a human infant or a human infant born prematurely. In another embodiment, the subject is a human with cystic fibrosis, bronchopulmonary dysplasia, congenital heart disease, congenital immunodeficiency or acquired immunodeficiency, a human who has had a bone marrow transplant, or an elderly human.

Various delivery systems are known and can be used to administer an F protein epitope of the invention or an anti-F protein epitope binder of the invention or a fragment thereof e.g., encapsulation in liposomes, microparticles, microcapsules, recombinant cells capable of expressing the antibody or antibody fragment, receptor-mediated endocytosis (see, e.g., Wu and Wu, 1987, *J. Biol. Chem.* 262:4429-4432), construction of a nucleic acid as part of a retroviral or other vector, etc. Methods of administering the F protein epitope of the invention or fragment thereof, or an anti-F protein epitope binder or fragment thereof or pharmaceutical composition of either or both, include but are not limited to, parenteral administration (e.g., intradermal, intramuscular, intraperitoneal, intravenous and subcutaneous), epidural, and mucosal (e.g., intranasal and oral routes). In a specific embodiment, anti-F peptide binders of the present invention or fragments thereof or pharmaceutical compositions comprising them, are administered intramuscularly, intravenously, or subcutaneously. The compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968, 5,985,320, 5,985,309, 5,934,272, 5,874,064, 5,855,913, 5,290,540, and 4,880,078; and PCT Publication Nos. WO 92/19244, WO 97/32572, WO 97/44013, WO 98/31346, and WO 99/66903, each of which is incorporated herein by reference their entirety. In a preferred embodiment, an antibody of the invention or fragment thereof, or composition of the invention is administered using Alkermes AIR™ pulmonary drug delivery technology (Alkermes, Inc., Cambridge, Mass.).

In a specific embodiment, it may be desirable to administer the compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. When administering a peptide or antibody of the invention or fragment thereof, care must be taken to use materials to which the antibody or antibody fragment does not absorb.

In another embodiment, the composition of the invention can be delivered in a vesicle, in particular a liposome (see Langer, 1990, *Science* 249:1527-1533; Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 317-327; see generally ibid.).

In yet another embodiment, the composition of the invention can be delivered in a controlled release or sustained release system. In one embodiment, a pump may be used to achieve controlled or sustained release (see Langer, supra; Sefton, 1987, *CRC Crit. Ref. Biomed. Eng.* 14:20; Buchwald et al., 1980, *Surgery* 88:507; Saudek et al., 1989, *N. Engl. J. Med.* 321:574, each of which are hereby incorporated by reference). In another embodiment, polymeric materials can be used to achieve controlled or sustained release of the F peptide or the antibodies of the invention or fragments thereof (see e.g., Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, N.Y. (1984); Ranger and Peppas, 1983, *J., Macromol. Sci. Rev. Macromol. Chem.* 23:61; see also Levy et al., 1985, *Science* 228:190; During et al., 1989, *Ann. Neurol.* 25:351; Howard et al., 1989, *J. Neurosurg.* 71:105); U.S. Pat. No. 5,679,377; U.S. Pat. No. 5,916,597; U.S. Pat. No. 5,912,015; U.S. Pat. No. 5,989,463; U.S. Pat. No. 5,128,326; PCT Publication No. WO 99/15154; and PCT Publication No. WO 99/20253 (each of these patents and publications are hereby incorporated by reference in their entirety). Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the therapeutic target, i.e., the lungs, thus requiring only a fraction of the systemic dose (see, e.g., Goodson, 1984, in *Medical Applications of Controlled Release*, supra, vol. 2, pp. 115-138, hereby incorporated by reference in its entirety).

The present invention also provides pharmaceutical compositions. Such compositions comprise a prophylactically or therapeutically effective amount of the F peptide or F peptide binder or a fragment thereof, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete)), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "*Remington's Pharmaceutical Sciences*" by E. W. Martin. Such compositions will contain a prophylactically or therapeutically effective amount of the antibody or fragment thereof, preferably in purified form, together with a suitable amount of carrier so as to provide the form for proper administration to the patient. The formulation should suit the mode of administration.

In a preferred embodiment, the pharmaceutical composition of the invention is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

The amount of the composition of the invention, which will be effective in the treatment, prevention, or amelioration of one or more symptoms associated with a RSV infection, can be determined by standard clinical techniques. For example, the dosage of the composition which will be effective in the treatment, prevention or amelioration of one or more symptoms associated with a RSV infection can be determined by administering the composition to a cotton rat, measuring the RSV titer after challenging the cotton rat with 105 pfu of RSV and comparing the RSV titer to that obtain for a cotton rat not administered the composition. Accordingly, a dosage that results in a 2 log decrease or a 99% reduction in RSV titer in the cotton rat challenged with $10^5$ pfu of RSV relative to the cotton rat challenged with $10^5$ pfu of RSV but not administered the composition is the dosage of the composition that can be administered to a human for the treatment, prevention or amelioration of symptoms associated with RSV infection. The dosage of the composition which will be effective in the treatment, prevention or amelioration of one or more symptoms associated with a RSV infection can be determined by administering the composition to an animal model (e.g., a cotton rat or monkey) and measuring the serum titer of binders (e.g., antibodies) or fragments thereof that specifically bind to the F peptide. In addition, in vitro assays may optionally be employed to help identify optimal dosage ranges.

The present invention provides kits that can be used in the above methods. In one embodiment, a kit comprises an anti-F protein epitope binder of the invention, preferably a purified antibody, in one or more containers. In an alterative embodiment, a kit comprises an anti-F protein epitope binder fragment. In a specific embodiment, the kits of the present invention contain a substantially isolated RSV antigen (e.g., an F protein epitope of the present invention) as a control. Preferably, the kits of the present invention further comprise a control antibody that does not react with an F protein epitope of the present invention or any other RSV antigen.

In another specific embodiment, the kits of the present invention contain a means for detecting the binding of a binder, e.g., an antibody, to the F peptides of the invention (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate). In specific embodiments, the kit may include a recombinantly produced or chemically synthesized F protein epitope of the present invention. The F protein provided in the kit may also be attached to a solid support. In a more specific embodiment the detecting means of the above-described kit includes a solid support to which an F protein epitope of the present invention is attached. Such a kit may also include a non-attached reporter-labeled anti-human antibody. In this embodiment, binding of the antibody to the RSV antigen can be detected by binding of the said reporter-labeled antibody.

EXAMPLES

Example 1

Selection of Monoclonal Antibody Resistant Mutants (MARMs) to RSV

Figure 2:
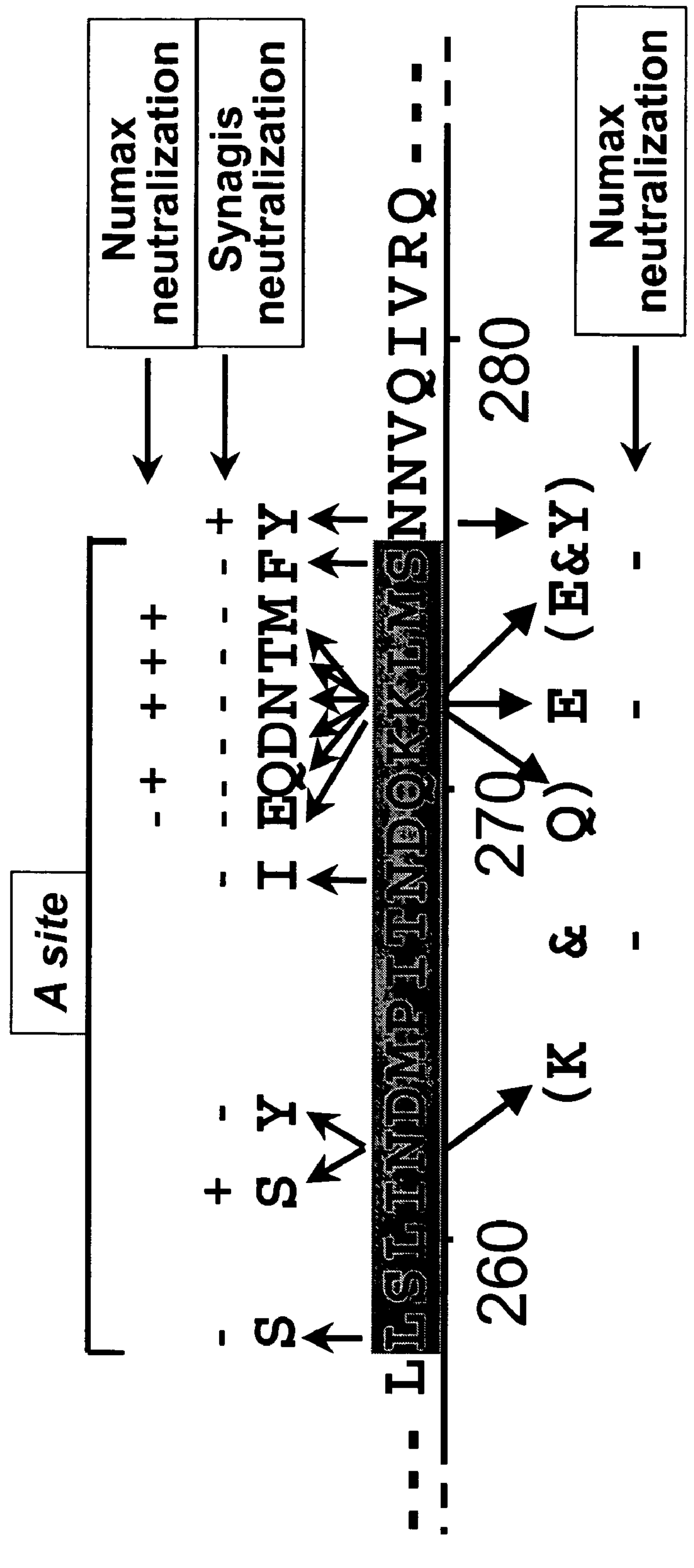

Hep-2 cells were infected in 24 well plates with RSV in the presence of an anti-RSV monoclonal antibody, such as, for instance, Synagis® (palivizumab) and/or Numax™ (motavizumab) or MEDI-524. The virus was passaged from wells which showed CPE two more times in the continued presence of the monoclonal antibody. The resulting plaques were purified two times in the presence of the monoclonal antibody. The virus was expanded to produce virus stock in the presence of the monoclonal antibody. Analysis of the viral mutants was performed by a microneutralization assay and IFA. Finally, the sequence of the mutant F protein was determined by standard methods. FIG. 2 shows the resulting MARM analysis for both Synagis® (palivizumab) and Numax™ (motavizumab). When the amino acid residue at position 272 was altered from a lysine (K) to a glutamic acid (E), both Synagis® and Numax™ longer neutralized RSV. All other mutations indicated at position 272 appear to eliminate the ability of Synagis® to neutralize RSV, while Numax™ appears to retain its ability to neutralize. Further, when a double mutation was made in the RSV F protein where the residue at position 272 was altered from a lysine (K) to a glutamine (Q) and residue 262 was altered from a asparagine (N) to a lysine (K), both Synagis® and Numax™ lost their ability to neutralize when the single mutant at K272Q did not knock out Numax™ neutralization. The results are summarized in Table 3. Antibody contact with residues 262 and 272 appears important.

TABLE 3

| Selection | MARM | Changes | Frequency | Nature of Changes | Neutraliz by Synagis ® ? | Neutraliz by Numax ™ ? |
|---|---|---|---|---|---|---|
| Synagis ® | B1 | K272N | 1/12 | Basic to uncharged, polar | No | Yes |
| Synagis ® | B2 | K272M | 7/12 | Basic to non-polar | No | Yes |
| Synagis ® | B7 | K272T | 2/12 | Basic to uncharged, polar | No | Yes |
| Synagis ® | B9 | K272Q | 2/12 | Basic to uncharged, polar | No | Yes |
| Synagis ® then A4b4 | #13 | N262K K272Q | 1/1 | Uncharged, polar to basic Basic to uncharged, polar | No | No |
| A4b4 | #6 | K272E | 4/5 | Basic to acidic | No | No |
| A4b4 | #10 | K272E N276Y | 1/5 | Basic to acidic Uncharged, polar to uncharged polar with bulky aromatic ring | No | No |
| Numax ™ | NuMARM3 | K272E | 19/19 | Basic to acidic | No | No |

Example 2

Binding Elisa of F-Peptides

Figure 3:
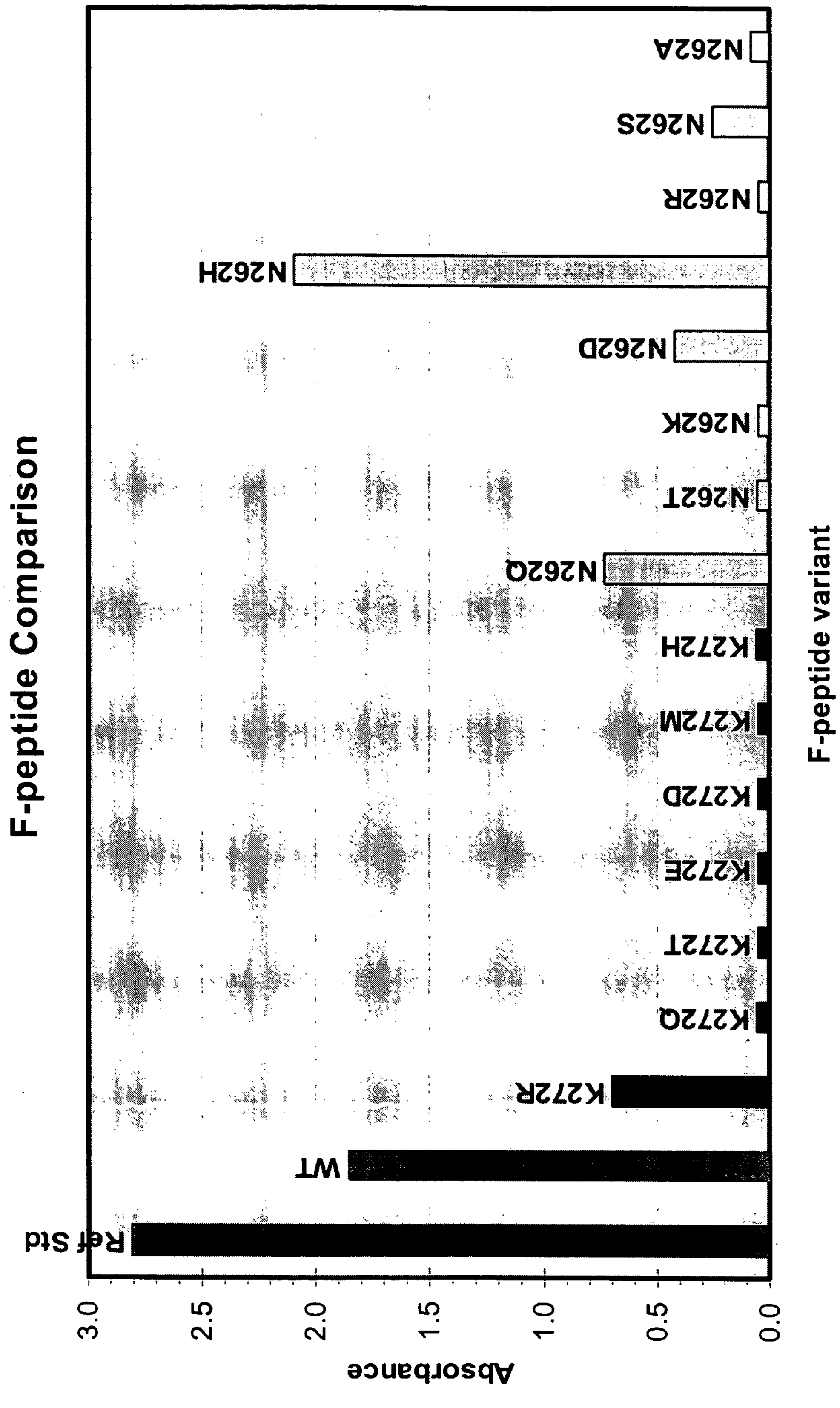
FIG. 3 shows the results of a binding ELISA comparing F peptides and wild-type F protein sequence binding to NUMAX™.

Based in part upon the results of the MARM analysis above, F peptides were synthesized (done by AnaSpec, Inc. San Jose, Calif.). Each well of the assay plate was coated with 50 ml/well of 4 mg/mL of a particular soluble RSV F-Peptide overnight at 2-8° C. After the plate was aspirated and washed with PBS/0.05% Tween-20 buffer, it was blocked by incubating with PBS/0.05% Tween-20/0.5% BSA buffer for one hour at ambient temperature. The plate was washed and MEDI-524 standard curve samples, test samples, MEDI-524 Reference Standard, and negative control were added to the washed plate. Following a one-hour incubation at ambient temperature, the plate was washed, and 50 ml per well of a goat anti-human IgG-HRP (horseradish peroxidase) at 1:16,000 dilution was added to the plate. After washing, 100 ml/well of 3,3',5,5'-tetramethylbenzidine (TMB) substrate was then added to the plate and incubated at ambient temperature protected from light for 10 minutes. The enzymatic reaction was stopped by adding 50 ml/well of 2N H2SO4, and the absorbance at 450 nm was measured using a microplate reader. The slope of the log-log transformation of the Reference Standard curve was compared with the historic Reference Standard slope range, and parallelism (90% confidence limit) of the test sample curve to the Reference Standard curve was tested. After meeting all system suitability requirements, as well as meeting the criteria of the parallelism test, the ED50 ratio of the test sample to Reference Standard was calculated, and the results were expressed as a percentage of the Reference Standard binding activity. FIG. 3 shows the results of this particular binding ELISA. The acceptable activity is 50-150% of Reference Standard binding. It appears that at position 262 of the F peptide, it is preferable that the amino acid be an H-bonding residue (in the wild-type, the residue is glutamine). At position 272, it appears preferable that the amino acid be a positively charged amino acid. Further, an F peptide with a histidine at position 262 appeared to bind Numax™ more tightly than a wild-type F protein epitope (SEQ ID NO.1).

Example 3

Biacore Kinetic Analysis

All studies were performed using Sensor Chip CM5 (Biacore AB, Uppsala, Sweden) which contains a carboxymethyl (CM) dextran matrix and a Biacore® 3000 surface plasmon resonance (SPR) biosensor (Biacore AB, Uppsala, Sweden).

Figure 4:
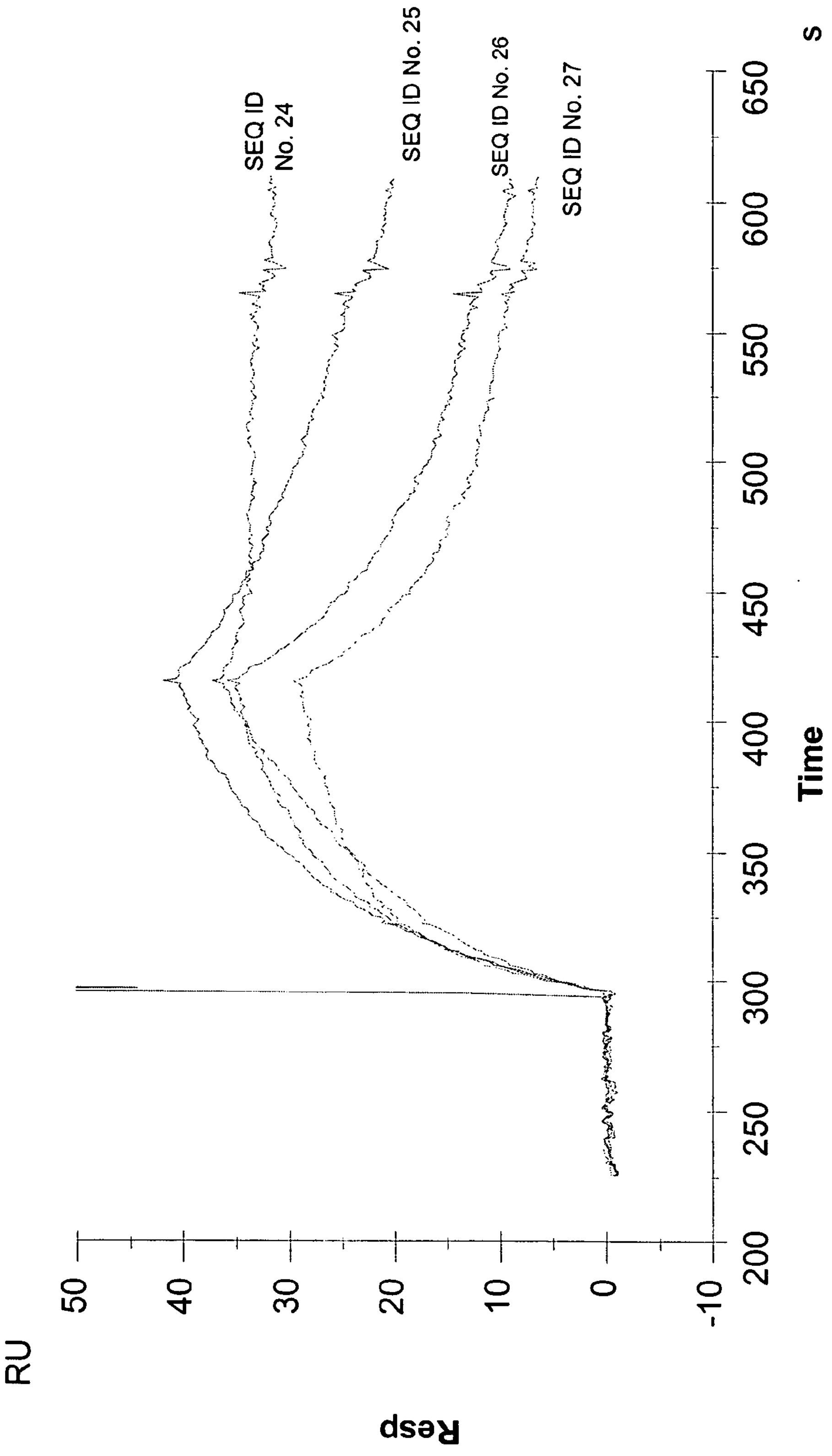
FIG. 4 shows BIAcore results to assess binding kinetics of various F peptides relative to the RSV F protein.

Numax™ was captured via a high-affinity interaction between the Fc portion of Numax™ and a goat anti-human IgG(Fc) (KPL, Inc., Gaithersburg, Md.). Goat anti-human IgG(Fc) was covalently attached to the CM dextran matrix using amine coupling chemistry. Two anti-human IgG(Fc)-specific surfaces were created. Numax™ was diluted to 10.9 μg/mL with HBS-EP and flowed for 1 min. across one of the anti-human IgG (Fc) surfaces at a flow rate of 5 μL/min. The other anti-human IgG(Fc) surface was used as a reference surface. F peptide was prepared by dilution in HBS-EP (0.01 M Hepes pH 7.4, 0.15 M NaCl, 3 mM EDTA, 0.005% surfactant P20) to a final concentration of 100 nM. F peptide was injected for 1 min. in a serial-flow manner across the reference surface and the Numax™-specific surface. Dissociation of bound F peptide was monitored for 2 min in the presence of HBS-EP. After this dissociation period, Numax™ and F peptide were removed with a 30-sec injection of 10 mM glycine pH 1.7 (Biacore AB, Uppsala, Sweden). Because of the removal of Numax™, it was necessary to create a new Numax™-specific surface prior to the injection of each F peptide. FIG. 4 graphically shows the results.

TABLE 4

Results of BIAcore Analysis

| Sample | $k_a$ | $k_d$ | $K_D$ |
|---|---|---|---|
| SEQ ID NO: 26 | 2.43E+05 | 5.52E−03 | 2.27E−08 |
| SEQ ID NO: 25 | 2.50E+05 | 1.81E−03 | 7.23E−09 |
| SEQ ID NO: 25 | 3.62E+05 | 1.97E−03 | 5.44E−09 |
| SEQ ID NO: 24 | 1.06E+05 | 2.42E−04 | 2.29E−09 |
| SEQ ID NO: 27 | 2.70E+05 | 5.50E−03 | 2.04E−08 |
| Numax Ref. Std. | 4.70E+05 | 1.88E−06 | 4.00E−12 |

Example 4

Evaluation of Binding Properties of F Peptides to Anti-RSV Antibody Using Isothermal Titration Calorimetry (ITC)

To evaluate the binding properties of the wild-type peptide (SEQ ID NO.28) to Numax™/MEDI-524 by using the ITC technique. The MEDI-524 Mab was titrated with SEQ ID NO.28 in the basis buffer 25 mM His, pH 6 at 10° C. SEQ ID NO.28: (MW=2732.14, no W, Y, or C). A working solution of 55 μM was prepared by diluting 30 μL of a 5 mg/mL peptide solution with 970 μL of 25 mM His, pH 6 buffer to be used for the ITC titrations. A 1.15 μM (0.1706 mg/ml) working solution of MEDI-524 was used for the experiments (MW 148400, A280=1.47). The results are as follows: (a) the binding strength is ~3 orders of magnitude lower compare to the SEQ ID NO.24 peptide; (b) 1 binding site was detected; (c) the binding constant was determined as: 4.36±0.5×106 M−1; (d) the binding enthalpy was determined to be: 4.8±0.1 Kcal M−1; and (e) stoichiometry: 4. FIG. 5 shows the results of the experiment graphically over time (in minutes).

To obtain binding constants for MEDI-524 Mab and MEDI-524 Fab fragments with F peptides constructed from F protein sequences, ITC was performed.

A note apart is the fact that the observed binding capacity (N) increases with the length of the peptide, indicating possibly an extra conformational factor in the binding event. The entropic contribution: For the peptides SEQ ID NOs.24 and 26, the entropic factor seems to be similar; the extra amino acids at the end of the N-terminal seems not to affect greatly the binding parameters. On the other hand, the elongation at the C-terminal seems to decrease slightly the binding enthalpy, the binding constant, as well as the entropic factor. The binding capacity seems to be increased in the cases where the 30-mer peptides were used (SEQ ID Nos. 25 and 26), when compare to the SEQ ID NO.24 peptide, possibly due to the longer extent of the whole peptides. The binding constant seems to be smaller (weaker) for both 30-mer peptides respect to the 26-mer. Since the entropic contribution did not change appreciably from the 26-mer to the 30-mer N terminal peptide (SEQ ID NO.26), could probably be proposed that the main driving force for the binding will be electrostatic, while for the 30-mer C-terminal peptide (SEQ ID NO.25), the decrease in both the enthalpy and entropy may lead to a more strong hydrophobic effect driven interaction.

TABLE 5

Peptide information

| Peptide | Sequence | MW |
|---|---|---|
| SEQ ID NO. 24 | NSELLSLINDMPITNDQKKLMSNN(X-orn)C | 2949.0000 |
| SEQ ID NO. 25 | NSELLSLIHDMPITNDQKKLMSNNVQIVRQ | 3479.0546 |
| SEQ ID NO. 26 | STYMLTNSELLSLIHDMPITNDQKKLMSNN | 3452.0001 |

TABLE 6

Titration Results of Medi-524 with peptides SEQ ID NO. 24, SEQ ID NO. 25, and SEQ ID NO. 26

| | SEQ ID NO. 24 | | SEQ ID NO. 25 | | SEQ ID NO. 26 | |
|---|---|---|---|---|---|---|
| At 18° C. | Mab | Fab | Mab | Fab | Mab* | Fab |
| $K_{diss}$ ($M^{-1}$) | $1.2 \times 10^7$ | $1.3 \times 10^7$ | $5.1 \times 10^6$ | $6.5 \times 10^6$ | $8.3 \times 10^6$* | $7.1 \times 10^6$ |
| $\Delta H_{binding}$ (Kcal/Mol) | −12.5 | −12.8 | −10.0 | −10.4 | −12.6* | −11.4 |
| N | 2.0 | 1.05 | 2.3 | 1.3 | 2.7* | 1.4 |
| $\Delta S_{binding}$ | −10.5 | −11.4 | −3.5 | −4.7 | −11.5* | −8.1 |

1 experiment only.

For this set of experiments, 0.172 gm/mL (1.16 μM-148.4 KDa) of MEDI-524 Mab and 0.088 mg/mL (1.88 μM-46.3 KDa) of MEDI-524 Fab, both in 25 mM His, pH 6.07 were used. On the other hand, 250 μL of 1 mg/mL of the different peptides dissolved in $H_2O$, were provided by ABC. The peptides were then diluted into the appropriate volume of buffer to give a final concentration of 50 μM. The ITC experiments were run at 18° C. with the macromolecule (Mab or Fab) in the cell, by doing ~26 injections of 10 μL of peptides, spaced 360 sec with constant stirring. The data fitting was accomplished by subtracting the average value of the few last injections as the buffer and unspecific heat of dilution contributions. RESULTS: The Mab shows binding capacity of 2, as expected by having 2 Fab segments, which in turns, shows only capacity for binding one peptide molecule per fragment.

Equivalents

Those skilled in the art will recognize, or be able to ascertain using no more than routine experimentation, many equivalents to the specific embodiments of the invention described herein. Such equivalents are intended to be encompassed by the following claims. All publications, patents and patent applications mentioned in this specification are herein incorporated by reference into the specification to the same extent as if each individual publication, patent or patent application was specifically and individually indicated to be incorporated herein by reference, particularly, a U.S. Provisional Application no. 60/718,719 filed concurrently on Sep. 21, 2005.

What is claimed is:

1. An RSV F peptide consisting of an amino acid sequence, wherein said amino acid sequence has the following structure:

$NSEL_{\alpha}SLI_{\beta}DMPIT_{\gamma}DQK_{\delta}LM_{\epsilon}NN$ (SEQ ID NO:34) where α may be either a leucine or a serine; where β may be an asparagine, a histidine, an alanine, a serine, an arginine, an aspartic acid, a lysine, a tyrosine, or a glutamine; where γ may be an asparagine or an isoleucine; where δ may be a glutamic acid, a glutamine, an aspartic acid, a threonine, a methionine, a lysine, or a tyrosine; and where ϵ may be a serine, a glutamic acid, or a phenylalanine.

2. An RSV F peptide consisting of an amino acid sequence with at least 90% identity to the full length of SEQ ID NO.: 1.

3. The RSV F peptide of claim 2, wherein said amino acid sequence is selected from the group consisting of SEQ ID Nos:1-28.

4. The RSV F peptide of claim 1, wherein said peptide is conjugated to a diagnostic agent.

5. The RSV F peptide of claim 2, wherein said peptide is conjugated to a diagnostic agent.

6. The RSV F peptide of claim 1, wherein said peptide is conjugated to a therapeutic agent.

7. The RSV F peptide of claim 2, wherein said peptide is conjugated to a therapeutic agent.

8. A fusion protein comprising the RSV F peptide of claim 1 and a heterologous polypeptide, wherein said heterologous polypeptide increases the serum half-life of said RSV F peptide.

9. A fusion protein comprising the RSV F peptide of claim 2 and a heterologous polypeptide, wherein said heterologous polypeptide increases the serum half-life of said RSV F peptide.

10. The fusion protein of claim 8, wherein said heterologous polypeptide is an IgG Fc domain peptide or serum albumin.

11. The fusion protein of claim 9, wherein said heterologous polypeptide is an IgG Fc domain peptide or serum albumin.

12. A PEGylated RSV F peptide, wherein said PEGylated RSV F peptide comprises the RSV F peptide of claim 1 conjugated to PEG.

13. A PEGylated RSV F peptide, wherein said PEGylated RSV F peptide comprises the RSV F peptide of claim 2 conjugated to PEG.

14. A composition comprising the RSV F peptide of claim 1, and a pharmaceutically acceptable carrier, wherein said composition can elicit an immune response.

15. A composition comprising the RSV F peptide of claim 2, and a pharmaceutically acceptable carrier, wherein said composition can elicit an immune response.

* * * * *

SEQUENCE LISTING

<160> NUMBER OF SEQ ID NOS: 34

<210> SEQ ID NO 1
<211> LENGTH: 24
<212> TYPE: PRT
<213> ORGANISM: respiratory syncytial virus

<400> SEQUENCE: 1

```
Asn Ser Glu Leu Leu Ser Leu Ile Asn Asp Met Pro Ile Thr Asn Asp
1               5                   10                  15

Gln Lys Lys Leu Met Ser Asn Asn
            20
```

<210> SEQ ID NO 2
<211> LENGTH: 24
<212> TYPE: PRT
<213> ORGANISM: Artificial Sequence
<220> FEATURE:
<223> OTHER INFORMATION: F peptide recombinantly derived from respiratory syncytial virus sequence

<400> SEQUENCE: 2

```
Asn Ser Glu Leu Leu Ser Leu Ile Asn Asp Met Pro Ile Thr Asn Asp
1               5                   10                  15

Gln Lys Arg Leu Met Ser Asn Asn
            20
```

<210> SEQ ID NO 3
<211> LENGTH: 24
<212> TYPE: PRT
<213> ORGANISM: Artificial Sequence
<220> FEATURE:
<223> OTHER INFORMATION: F peptide recombinantly derived from respiratory syncytial virus sequence

<400> SEQUENCE: 3

```
Asn Ser Glu Leu Leu Ser Leu Ile Asn Asp Met Pro Ile Thr Asn Asp
1               5                   10                  15

Gln Lys Gln Leu Met Ser Asn Asn
            20
```

<210> SEQ ID NO 4
<211> LENGTH: 24
<212> TYPE: PRT
<213> ORGANISM: Artificial Sequence
<220> FEATURE:
<223> OTHER INFORMATION: F peptide recombinantly derived from respiratory syncytial virus sequence

<400> SEQUENCE: 4

```
Asn Ser Glu Leu Leu Ser Leu Ile Asn Asp Met Pro Ile Thr Asn Asp
1               5                   10                  15

Gln Lys Thr Leu Met Ser Asn Asn
            20
```

<210> SEQ ID NO 5
<211> LENGTH: 24
<212> TYPE: PRT
<213> ORGANISM: Artificial Sequence
<220> FEATURE:
<223> OTHER INFORMATION: F peptide recombinantly derived from respiratory syncytial virus sequence

<400> SEQUENCE: 5

-continued

```
Asn Ser Glu Leu Leu Ser Leu Ile Asn Asp Met Pro Ile Thr Asn Asp
1               5                   10                  15

Gln Lys Glu Leu Met Ser Asn Asn
            20


<210> SEQ ID NO 6
<211> LENGTH: 24
<212> TYPE: PRT
<213> ORGANISM: Artificial Sequence
<220> FEATURE:
<223> OTHER INFORMATION: F peptide recombinantly derived from
      respiratory syncytial virus sequence

<400> SEQUENCE: 6

Asn Ser Glu Leu Leu Ser Leu Ile Asn Asp Met Pro Ile Thr Asn Asp
1               5                   10                  15

Gln Lys Asp Leu Met Ser Asn Asn
            20


<210> SEQ ID NO 7
<211> LENGTH: 24
<212> TYPE: PRT
<213> ORGANISM: Artificial Sequence
<220> FEATURE:
<223> OTHER INFORMATION: F peptide recombinantly derived from
      respiratory syncytial virus sequence

<400> SEQUENCE: 7

Asn Ser Glu Leu Leu Ser Leu Ile Asn Asp Met Pro Ile Thr Asn Asp
1               5                   10                  15

Gln Lys Met Leu Met Ser Asn Asn
            20


<210> SEQ ID NO 8
<211> LENGTH: 24
<212> TYPE: PRT
<213> ORGANISM: Artificial Sequence
<220> FEATURE:
<223> OTHER INFORMATION: F peptide recombinantly derived from
      respiratory syncytial virus sequence

<400> SEQUENCE: 8

Asn Ser Glu Leu Leu Ser Leu Ile Asn Asp Met Pro Ile Thr Asn Asp
1               5                   10                  15

Gln Lys His Leu Met Ser Asn Asn
            20


<210> SEQ ID NO 9
<211> LENGTH: 24
<212> TYPE: PRT
<213> ORGANISM: Artificial Sequence
<220> FEATURE:
<223> OTHER INFORMATION: F peptide recombinantly derived from
      respiratory syncytial virus sequence

<400> SEQUENCE: 9

Asn Ser Glu Leu Leu Ser Leu Ile Gln Asp Met Pro Ile Thr Asn Asp
1               5                   10                  15

Gln Lys Lys Leu Met Ser Asn Asn
            20


<210> SEQ ID NO 10
<211> LENGTH: 24
<212> TYPE: PRT
```

-continued

<213> ORGANISM: respiratory syncytial virus

<400> SEQUENCE: 10

Asn Ser Glu Leu Leu Ser Leu Ile Tyr Asp Met Pro Ile Thr Asn Asp
1 5 10 15

Gln Lys Lys Leu Met Ser Asn Asn
20

<210> SEQ ID NO 11
<211> LENGTH: 24
<212> TYPE: PRT
<213> ORGANISM: Artificial Sequence
<220> FEATURE:
<223> OTHER INFORMATION: F peptide recombinantly derived from respiratory syncytial virus sequence

<400> SEQUENCE: 11

Asn Ser Glu Leu Leu Ser Leu Ile Lys Asp Met Pro Ile Thr Asn Asp
1 5 10 15

Gln Lys Lys Leu Met Ser Asn Asn
20

<210> SEQ ID NO 12
<211> LENGTH: 24
<212> TYPE: PRT
<213> ORGANISM: Artificial Sequence
<220> FEATURE:
<223> OTHER INFORMATION: F peptide recombinantly derived from respiratory syncytial virus sequence

<400> SEQUENCE: 12

Asn Ser Glu Leu Leu Ser Leu Ile Asp Asp Met Pro Ile Thr Asn Asp
1 5 10 15

Gln Lys Lys Leu Met Ser Asn Asn
20

<210> SEQ ID NO 13
<211> LENGTH: 24
<212> TYPE: PRT
<213> ORGANISM: Artificial Sequence
<220> FEATURE:
<223> OTHER INFORMATION: F peptide recombinantly derived from respiratory syncytial virus sequence

<400> SEQUENCE: 13

Asn Ser Glu Leu Leu Ser Leu Ile His Asp Met Pro Ile Thr Asn Asp
1 5 10 15

Gln Lys Lys Leu Met Ser Asn Asn
20

<210> SEQ ID NO 14
<211> LENGTH: 24
<212> TYPE: PRT
<213> ORGANISM: Artificial Sequence
<220> FEATURE:
<223> OTHER INFORMATION: F peptide recombinantly derived from respiratory syncytial virus sequence

<400> SEQUENCE: 14

Asn Ser Glu Leu Leu Ser Leu Ile Arg Asp Met Pro Ile Thr Asn Asp
1 5 10 15

Gln Lys Lys Leu Met Ser Asn Asn
20

-continued

<210> SEQ ID NO 15
<211> LENGTH: 24
<212> TYPE: PRT
<213> ORGANISM: Artificial Sequence
<220> FEATURE:
<223> OTHER INFORMATION: F peptide recombinantly derived from respiratory syncytial virus sequence

<400> SEQUENCE: 15

Asn Ser Glu Leu Leu Ser Leu Ile Ser Asp Met Pro Ile Thr Asn Asp
1 5 10 15

Gln Lys Lys Leu Met Ser Asn Asn
20

<210> SEQ ID NO 16
<211> LENGTH: 24
<212> TYPE: PRT
<213> ORGANISM: Artificial Sequence
<220> FEATURE:
<223> OTHER INFORMATION: F peptide recombinantly derived from respiratory syncytial virus sequence

<400> SEQUENCE: 16

Asn Ser Glu Leu Leu Ser Leu Ile Ala Asp Met Pro Ile Thr Asn Asp
1 5 10 15

Gln Lys Lys Leu Met Ser Asn Asn
20

<210> SEQ ID NO 17
<211> LENGTH: 24
<212> TYPE: PRT
<213> ORGANISM: Artificial Sequence
<220> FEATURE:
<223> OTHER INFORMATION: F peptide recombinantly derived from respiratory syncytial virus sequence

<400> SEQUENCE: 17

Asn Ser Glu Leu Ser Ser Leu Ile Asn Asp Met Pro Ile Thr Asn Asp
1 5 10 15

Gln Lys Lys Leu Met Ser Asn Asn
20

<210> SEQ ID NO 18
<211> LENGTH: 24
<212> TYPE: PRT
<213> ORGANISM: Artificial Sequence
<220> FEATURE:
<223> OTHER INFORMATION: F peptide recombinantly derived from respiratory syncytial virus sequence

<400> SEQUENCE: 18

Asn Ser Glu Leu Leu Ser Leu Ile Asn Asp Met Pro Ile Thr Asn Asp
1 5 10 15

Gln Lys Tyr Leu Met Ser Asn Asn
20

<210> SEQ ID NO 19
<211> LENGTH: 24
<212> TYPE: PRT
<213> ORGANISM: Artificial Sequence
<220> FEATURE:
<223> OTHER INFORMATION: F peptide recombinantly derived from respiratory syncytial virus sequence

<400> SEQUENCE: 19

Asn Ser Glu Leu Leu Ser Leu Ile Asn Asp Met Pro Ile Thr Ile Asp

-continued

```
1               5                   10                  15

Gln Lys Lys Leu Met Ser Asn Asn
            20


<210> SEQ ID NO 20
<211> LENGTH: 24
<212> TYPE: PRT
<213> ORGANISM: Artificial Sequence
<220> FEATURE:
<223> OTHER INFORMATION: F peptide recombinantly derived from
      respiratory syncytial virus sequence

<400> SEQUENCE: 20

Asn Ser Glu Leu Leu Ser Leu Ile Asn Asp Met Pro Ile Thr Asn Asp
1               5                   10                  15

Gln Lys Asn Leu Met Ser Asn Asn
            20


<210> SEQ ID NO 21
<211> LENGTH: 24
<212> TYPE: PRT
<213> ORGANISM: Artificial Sequence
<220> FEATURE:
<223> OTHER INFORMATION: F peptide recombinantly derived from
      respiratory syncytial virus sequence

<400> SEQUENCE: 21

Asn Ser Glu Leu Leu Ser Leu Ile Asn Asp Met Pro Ile Thr Asn Asp
1               5                   10                  15

Gln Lys Lys Leu Met Phe Asn Asn
            20


<210> SEQ ID NO 22
<211> LENGTH: 24
<212> TYPE: PRT
<213> ORGANISM: Artificial Sequence
<220> FEATURE:
<223> OTHER INFORMATION: F peptide recombinantly derived from
      respiratory syncytial virus sequence

<400> SEQUENCE: 22

Asn Ser Glu Leu Leu Ser Leu Ile Asn Asp Met Pro Ile Thr Asn Asp
1               5                   10                  15

Gln Lys Lys Leu Met Ser Glu Asn
            20


<210> SEQ ID NO 23
<211> LENGTH: 24
<212> TYPE: PRT
<213> ORGANISM: Artificial Sequence
<220> FEATURE:
<223> OTHER INFORMATION: F peptide recombinantly derived from
      respiratory syncytial virus sequence

<400> SEQUENCE: 23

Asn Ser Glu Leu Leu Ser Leu Ile Asn Asp Met Pro Ile Thr Asn Asp
1               5                   10                  15

Gln Lys Lys Leu Met Ser Tyr Asn
            20


<210> SEQ ID NO 24
<211> LENGTH: 27
<212> TYPE: PRT
<213> ORGANISM: Artificial Sequence
<220> FEATURE:
```

-continued

```
<223> OTHER INFORMATION: F peptide recombinantly derived from
      respiratory syncytial virus sequence
<220> FEATURE:
<221> NAME/KEY: misc_feature
<222> LOCATION: (25)..(26)
<223> OTHER INFORMATION: Xaa can be any naturally occurring amino acid

<400> SEQUENCE: 24

Asn Ser Glu Leu Leu Ser Leu Ile Asn Asp Met Pro Ile Thr Asn Asp
1               5                   10                  15

Gln Lys Lys Leu Met Ser Asn Asn Xaa Xaa Cys
            20                  25


<210> SEQ ID NO 25
<211> LENGTH: 30
<212> TYPE: PRT
<213> ORGANISM: Artificial Sequence
<220> FEATURE:
<223> OTHER INFORMATION: F peptide recombinantly derived from
      respiratory syncytial virus sequence

<400> SEQUENCE: 25

Asn Ser Glu Leu Leu Ser Leu Ile His Asp Met Pro Ile Thr Asn Asp
1               5                   10                  15

Gln Lys Lys Leu Met Ser Asn Asn Val Gln Ile Val Arg Gln
            20                  25                  30


<210> SEQ ID NO 26
<211> LENGTH: 30
<212> TYPE: PRT
<213> ORGANISM: Artificial Sequence
<220> FEATURE:
<223> OTHER INFORMATION: F peptide recombinantly derived from
      respiratory syncytial virus sequence

<400> SEQUENCE: 26

Ser Thr Tyr Met Leu Thr Asn Ser Glu Leu Leu Ser Leu Ile His Asp
1               5                   10                  15

Met Pro Ile Thr Asn Asp Gln Lys Lys Leu Met Ser Asn Asn
            20                  25                  30


<210> SEQ ID NO 27
<211> LENGTH: 27
<212> TYPE: PRT
<213> ORGANISM: Artificial Sequence
<220> FEATURE:
<223> OTHER INFORMATION: F peptide recombinantly derived from
      respiratory syncytial virus sequence

<400> SEQUENCE: 27

Asn Ser Glu Leu Leu Ser Leu Ile Asn Asp Met Pro Ile Thr Asn Asp
1               5                   10                  15

Gln Lys Lys Leu Met Ser Asn Asn Cys Asn His
            20                  25


<210> SEQ ID NO 28
<211> LENGTH: 26
<212> TYPE: PRT
<213> ORGANISM: Artificial Sequence
<220> FEATURE:
<223> OTHER INFORMATION: F peptide recombinantly derived from
      respiratory syncytial virus sequence

<400> SEQUENCE: 28

Asn Ser Glu Leu Leu Ser Leu Ile Asn Asp Met Pro Ile Thr Asn Asp
1               5                   10                  15
```

-continued

```
Gln Lys Lys Leu Met Ser Asn Asn Asn His
            20                  25


<210> SEQ ID NO 29
<211> LENGTH: 575
<212> TYPE: PRT
<213> ORGANISM: respiratory syncytial virus

<400> SEQUENCE: 29

Met Glu Leu Pro Ile Leu Lys Ala Asn Ala Ile Thr Thr Ile Leu Ala
1               5                   10                  15

Ala Val Thr Phe Cys Phe Ala Ser Ser Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Ala Asn Asn Arg Ala Arg Arg Glu Leu Pro
            100                 105                 110

Arg Phe Met Asn Tyr Thr Leu Asn Asn Thr Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Thr Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Arg Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
```

-continued

```
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Cys Tyr Gly Lys Thr Lys Cys Thr Ala Ser Asn Lys Asn Arg Cys Ile
            420                 425                 430

Ile Lys Thr Phe Ser Asn Gly Cys Asp Tyr Ala Ser Asn Lys Gly Val
        435                 440                 445

Asp Thr Val Ser Val Gly Asn Thr Leu Tyr Tyr Val Asn Lys Gln Glu
    450                 455                 460

Gly Lys Ser Leu Tyr Val Lys Gly Glu Pro Ile Ile Asn Phe Tyr Thr
465                 470                 475                 480

Pro Leu Val Phe Pro Ser Asp Glu Phe Asp Ala Ser Ile Ser Gln Val
                485                 490                 495

Asn Glu Lys Ile Asn Gln Ser Leu Ala Phe Ile Arg Lys Ser Asp Glu
            500                 505                 510

Leu Leu His His Val Asn Ala Gly Lys Ser Thr Thr Asn Ile Met Ile
        515                 520                 525

Thr Thr Ile Ile Ile Val Ile Ile Val Ile Leu Leu Ser Leu Ile Ala
    530                 535                 540

Val Gly Leu Leu Leu Tyr Cys Lys Ala Arg Ser Thr Pro Val Thr Leu
545                 550                 555                 560

Ser Lys Asp Gln Leu Ser Gly Ile Asn Asn Ile Ala Phe Ser Asn
                565                 570                 575


<210> SEQ ID NO 30
<211> LENGTH: 106
<212> TYPE: PRT
<213> ORGANISM: Artificial Sequence
<220> FEATURE:
<223> OTHER INFORMATION: Variable light chain region of palivizumab

<400> SEQUENCE: 30

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys
            100                 105


<210> SEQ ID NO 31
<211> LENGTH: 120
<212> TYPE: PRT
<213> ORGANISM: Artificial Sequence
<220> FEATURE:
<223> OTHER INFORMATION: Variable heavy chain region of palivizumab
```

-continued

<400> SEQUENCE: 31

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys Asp Tyr Asn Pro Ser
    50                  55                  60

Leu Lys Ser Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Ser Met Ile Thr Asn Trp Tyr Phe Asp Val Trp Gly Ala
            100                 105                 110

Gly Thr Thr Val Thr Val Ser Ser
        115                 120
```

<210> SEQ ID NO 32
<211> LENGTH: 106
<212> TYPE: PRT
<213> ORGANISM: Artificial Sequence
<220> FEATURE:
<223> OTHER INFORMATION: Variable light chain region of motavizumab

<400> SEQUENCE: 32

```
Asp Ile Gln Met Thr Gln Ser Pro Ser Thr Leu Ser Ala Ser Val Gly
1               5                   10                  15

Asp Arg Val Thr Ile Thr Cys Ser Ala Ser Ser Arg Val Gly Tyr Met
            20                  25                  30

His Trp Tyr Gln Gln Lys Pro Gly Lys Ala Pro Lys Leu Leu Ile Tyr
        35                  40                  45

Asp Thr Ser Lys Leu Asp Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Val Glu Ile Lys
            100                 105
```

<210> SEQ ID NO 33
<211> LENGTH: 120
<212> TYPE: PRT
<213> ORGANISM: Artificial Sequence
<220> FEATURE:
<223> OTHER INFORMATION: Variable heavy chain region of motavizumab

<400> SEQUENCE: 33

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ala
            20                  25                  30

Gly Met Ser Val Gly Trp Ile Arg Gln Pro Pro Gly Lys Ala Leu Glu
        35                  40                  45

Trp Leu Ala Asp Ile Trp Trp Asp Asp Lys Lys His Tyr Asn Pro Ser
    50                  55                  60
```

-continued

```
Leu Lys Asp Arg Leu Thr Ile Ser Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala Arg Asp Met Ile Phe Asn Phe Tyr Phe Asp Val Trp Gly Gln
            100                 105                 110

Gly Thr Thr Val Thr Val Ser Ser
        115                 120


<210> SEQ ID NO 34
<211> LENGTH: 24
<212> TYPE: PRT
<213> ORGANISM: Artificial Sequence
<220> FEATURE:
<223> OTHER INFORMATION: F peptide recombinantly derived from
      respiratory syncytial virus sequence
<220> FEATURE:
<221> NAME/KEY: misc_feature
<222> LOCATION: (5), (9), (15), (19), (22)
<223> OTHER INFORMATION: Xaa can be any naturally occurring amino acid

<400> SEQUENCE: 34

Asn Ser Glu Leu Xaa Ser Leu Ile Xaa Asp Met Pro Ile Thr Xaa Asp
1               5                   10                  15

Gln Lys Xaa Leu Met Xaa Glu Asn
            20              24
```